(12) United States Patent
Stone

(10) Patent No.: US 8,236,301 B2
(45) Date of Patent: Aug. 7, 2012

(54) LUMICAN PROTEOGLYCAN IN THE DIAGNOSIS AND TREATMENT OF ATHEROSCLEROSIS

(75) Inventor: James R. Stone, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 839 days.

(21) Appl. No.: 11/918,621

(22) PCT Filed: May 18, 2006

(86) PCT No.: PCT/US2006/019505
§ 371 (c)(1),
(2), (4) Date: Nov. 19, 2008

(87) PCT Pub. No.: WO2006/125171
PCT Pub. Date: Nov. 23, 2006

(65) Prior Publication Data
US 2009/0123457 A1    May 14, 2009

Related U.S. Application Data

(60) Provisional application No. 60/682,177, filed on May 18, 2005.

(51) Int. Cl.
*A61K 38/00*    (2006.01)
*A61K 39/395*    (2006.01)

(52) U.S. Cl. ...................... 424/94.5; 424/9.1; 424/130.1

(58) Field of Classification Search ............... 424/130.1, 424/9.1, 94.5; 436/87
See application file for complete search history.

(56) References Cited

OTHER PUBLICATIONS

WO-FORM PCT/ISA/210, Jun. 10, 2008, ISR.
WO-PCT/ISA/237, Jun. 10, 2008, Written Opinion.
Antonsson et al., Postranslational Modifications of Fibromodulin, The Journal of Biological Chemistry, Sep. 5, 1991, vol. 266, No. 25, pp. 16859-16861, especially p. 16860.
Fabunmi et al., Expression of Tissue Inhibitor of Metalloproteinases-3 in Human Atheroma and Regulation in Lesion-Associated calls: A Potential Protective Mechanism in Plaque Stability, Circulation Research, 1998, vol. 83, pp. 270-278, whole document.
Apte et al., The Gene Structure of Tissue Inhibitor of Metalloproteinases (TIMP-3) and its Inhibitory Activities Define the Distinct TIMP Gene Family, The Journal of Biological Chemistry, Jun. 16, 1995, vol. 270, No. 24, pp. 14313-14318, whole document.
Li et al., Cleavage of Lumican by Membrane-Type Matrix Metalloproteinase-1 Abrogates This Proteoglycan-Mediated Suppression of Tumor Cell Colony Formation in Soft Agar, Cancer Research Oct. 1, 2004, vol. 64, pp. 7058-7064, whole document.

*Primary Examiner* — Chih-Min Kam
(74) *Attorney, Agent, or Firm* — Edwards Wildman Palmer LLP; Peter C. Lauro, Esq.; Richard B. Emmons

(57) ABSTRACT

The invention relates to methods of reducing formation of atheromas and methods of treating atherosclerotic lesions and/or atherosclerosis by reducing the amount of lumican proteglycan in the intima or an artery or in the lesion. The invention also relates to methods of identifying subjects having or at risk of having atherosclerosis comprising detecting an increased amount of lumican proteoglycan in a subject.

12 Claims, 17 Drawing Sheets

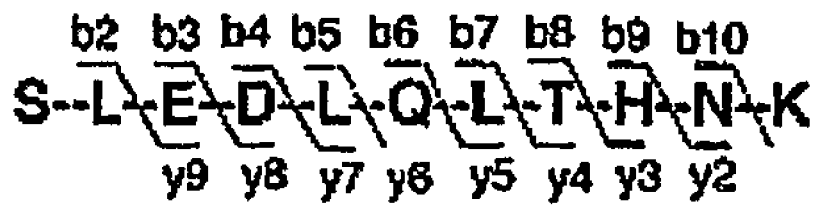
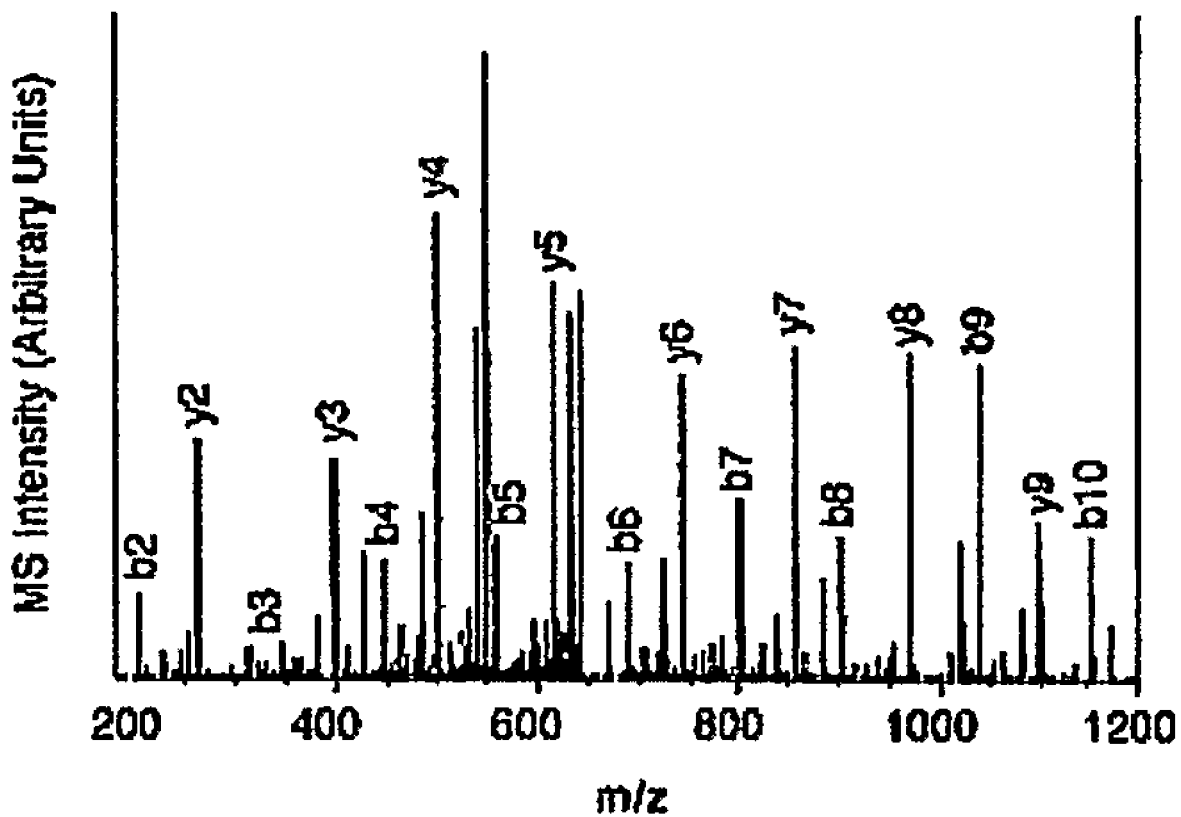
FIG. 5D

FIG. 6A FIG. 6B
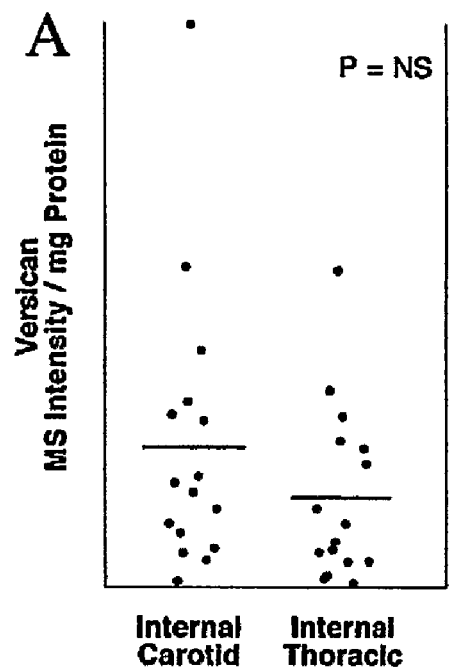 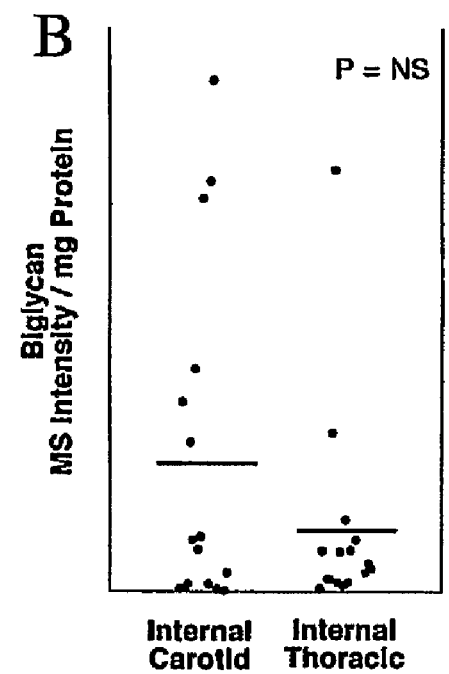
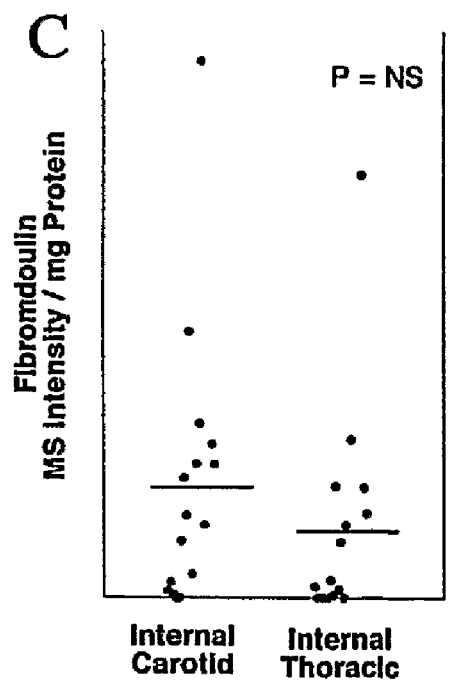 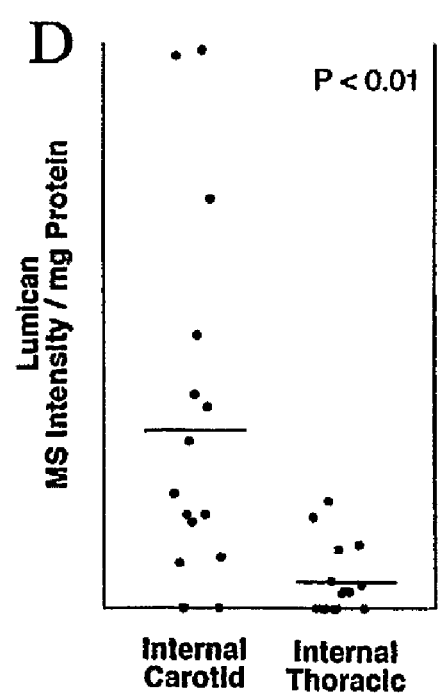
FIG. 6C FIG. 6D

SEQUENCE LISTING

<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Proteoglycan peptides

<400> SEQUENCE: 1

```
Leu Leu Ala Ser Asp Ala Gly Leu Tyr Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Proteoglycan peptide

<400> SEQUENCE: 2

Leu Ala Thr Val Gly Glu Leu Gln Ala Ala Trp Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Proteoglycan peptide

<400> SEQUENCE: 3

Glu Thr Thr Val Leu Val Ala Gln Asn Gly Asn Ile Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Proteoglycan peptide

<400> SEQUENCE: 4

Leu Gly Leu Gly His Asn Gln Ile Arg
1               5

<210> SEQ ID NO 5
<211> LENGTH: 13
<212> TYPE: PRT
<213> ORGANISM: Artificial Sequence
<220> FEATURE:
<223> OTHER INFORMATION: Proteoglycan peptide

<400> SEQUENCE: 5

Ser Ser Gly Ile Glu Asn Gly Ala Phe Gln Gly Met Lys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Proteoglycan peptide

<400> SEQUENCE: 6

Ser Ile Glu Tyr Ser Pro Gln Leu Glu Asp Ala Gly Ser Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Proteoglycan peptide

<400> SEQUENCE: 7

Leu Glu Gly Asp Thr Leu Ile Ile Pro Arg
1               5                   10
```

```
<210> SEQ ID NO 8
<211> LENGTH: 11
<212> TYPE: PRT
<213> ORGANISM: Artificial Sequence
<220> FEATURE:
<223> OTHER INFORMATION: Proteoglycan peptide

<400> SEQUENCE: 8

Ser Leu Glu Asp Leu Gln Leu Ile His Asn Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Proteoglycan peptide

<400> SEQUENCE: 9

Leu Lys Glu Asp Ala Val Ser Ala Ala Phe Lys
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Proteoglycan peptide

<400> SEQUENCE: 10

Ile Pro Pro Val Asn Thr Asn Leu Glu Asn Leu Tyr Leu Leu Gln Gly
1               5                   10                  15

Asn Arg

<210> SEQ ID NO 11
<211> LENGTH: 8
<212> TYPE: PRT
<213> ORGANISM: Artificial Sequence
<220> FEATURE:
<223> OTHER INFORMATION: Proteoglycan peptide

<400> SEQUENCE: 11

Tyr Leu Pro Phe Val Pro Ser Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Proteoglycan peptide

<400> SEQUENCE: 12

Glu Val Val Leu Leu Val Ala Thr Glu Gly Arg
1               5                   10
```

LUMICAN PROTEOGLYCAN IN THE DIAGNOSIS AND TREATMENT OF ATHEROSCLEROSIS

This application is the U.S. national phase application, pursuant to 35 U.S.C. §371, of PCT international application Ser. No. PCT/US2006/019505, filed May 18, 2006, designating the United States and published in English on Nov. 23, 2006 as publication no. WO 2006/125171 A2, which claims priority to U.S. provisional application Ser. No. 60/682,177, filed May 18, 2005. The entire contents of the aforementioned patent applications are incorporated herein by this reference.

RELATED APPLICATIONS/PATENTS & INCORPORATION BY REFERENCE

This application claims priority to U.S. application Ser. No. 60/682,177, filed on May 18, 2005, the contents of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF POTENTIAL GOVERNMENT INTEREST

The United States government may have certain rights in this invention by virtue of grant numbers HL074324 from the National Institutes of Health. Accordingly, the United States Government may have certain rights to this invention.

BACKGROUND OF THE INVENTION

Despite our advances in understanding risk factors for atherosclerosis, this disease remains the leading cause of death in western countries. This is in part a result of our current limited understanding of the specific pathophysiological mechanisms underlying the disease.

In humans, it is clear that atherosclerotic lesions develop at sites of pre-existing intimal thickening, or intimal hyperplasia (Schwartz et al. (1995) *Circulation Research* 77, 445-465; Ikari et al. (1999) *Arteriosclerosis, Thrombosis, and Vascular Biology* 19, 2036-2040; Schwartz (1999) *Circulation Research* 77, 445-465; Kiechl S. et al. (1999) *Arteriosclerosis, Thrombosis, and Vascular Biology* 19, 1484-1490; Nakashima et al. (2002) *Virchows Archives* 441, 279-288; Tracy (2003) Kluwer Acadmeic Publishers, Dordreclt, The Netherlands.). These pre-atherosclerotic lesions are typically eccentric and often located immediately distal to branch sites in the vasculature. The eccentric nature of these lesions and their location near branch sites both suggest that altered shear forces are a predominant etiological factor in their formation. Furthermore, it is clear that applying such altered shear forces to cultured endothelial cells in vitro, does in fact alter the phenotype of these cells, to a phenotype that would be more likely to promote the development of atherosclerosis (Davies (1995) *Physiological Reviews* 75, 519-160; Garcia-Cardena et al. (2001) *Proceedings of the National Academy of Sciences USA* 98, 4478-4485; Traub & Berk (1998) *Arterioscler. Thromb. Vasc. Biol.* 18, 677-685.).

These pre-atherosclerotic lesions are composed primarily of smooth muscle cells and abundant proteoglycan-rich extracellular matrix with scattered macrophages (Stary et al. (1992) *Circulation* 85, 391-405). Within these thickened intimal lesions, macrophages (and to a lesser extent smooth muscle cells) form foam cells secondary to ingestion of lipoproteins retained in the intima (Stary et al. (1994) *Circulation* 89, 2462-2478). Although these early lesions form quite frequently even in infancy, they appear to be readily reversible (Stary (2000) *American Journal of Clinical Nutrition* 72(Suppl.) 1297S-1306S; Stary (2003) *Atlas of atherosclerosis progression and regression*, $2^{nd}$ edition, Parthenon Publishing Group, New York). Thus, it appears that the predominant irreversible (or limitedly reversible) step, committing a vessel to clinically relevant atherosclerosis in humans, is the development of a necrotic/lipid core within this hyperplastic thickened intima.

Currently it is unclear why intimal hyperplasia progresses to atherosclerosis much more readily at some locations than at other locations. Along this line of investigation, much attention has been focused on the proteoglycans composing the extracellular matrix of the thickened intima. Proteoglycans have been proposed to play a direct role in atherosclerosis both by binding and retaining lipoproteins in the vessel wall and by regulating vascular cell growth (Berenson et al. (1985) *Annals of the New York Academy of Sciences* 454, 69-78; Camejo et al. (1990) *European Heart Journal* 11 (Suppl. E), 164-173; Camejo et al. (1993) *Journal of Biological Chemistry* 268, 14131-14137; Pentikäinen et al. (1997) *Journal of Biological Chemistry* 272, 7633-7638.; Steele et al. (1987) *Atherosclerosis* 65, 51-62.; Alavi et al. (1989) *American Journal of Pathology* 134, 287-294; Hurt-Camejo et al. (1997) *Arteriosclerosis, Thrombosis, and Vascular Biology* 17, 1011-1017; Camejo et al. (1998) *Atherosclerosis* 139, 205-222; Goldberg et al. (1998) *Journal of Biological Chemistry* 273, 35355-35361; Borén et al. (1998) *Journal of Clinical Investigation* 101, 2658-2664; Völker et al. (1990) *European Heart Journal* 11(Suppl. E), 29-40; Skålén et al. (2002) *Nature* 417, 750-754.). For a number of years it has been suggested that variations in the intimal proteoglycan composition could in part explain the marked differences in atherosclerosis susceptibility between different sites in the vasculature (Tracy (2003)).

Lumican is a member of the small-leucine-rich (SLR) family of proteoglycans. Based on sequence homology, this family is divided into three classes (Iozzo (1999) *Journal of Biological Chemistry* 274, 18843-18846). Class I SLR proteoglycans consist of decorin and biglycan, and contain chondroitin/dermatan sulfate glycosaminoglycan (GAG) side chains. In contrast, class II SLR proteoglycans include lumican, fibromodulin, PRELP, keratocan and osteoadherin and contain keratan sulfate GAG side chains. The Class III SLR proteoglycans consist of epiphycan and mimecan, of which the former may contain chondroitin/dermatan sulfate GAG side chains and the latter may contain keratan sulfate GAG side chains. Lumican was so named after first being discovered to be present at high levels in the cornea, where it plays an important role in maintaining corneal transparency (Blochberger et al. (1992) *The Journal of Biological Chemistry* 267, 347-352; Funderburgh et al. (1991) *Journal of*

Biological Chemistry 266, 24773-24777; Funderburgh et al. (1993) The Journal of Biological Chemistry 268. 11874-11880). Lumican is in fact the most abundant keratan sulfate proteoglycan in corneal stroma. In the cornea, lumican maintains corneal transparency predominantly through the proper ordering of collagen, but also likely by inhibiting cellular proliferation and thus contributing to the low cellularity and immune-privileged nature of the cornea (Vijayagopal et al. (1996) Atherosclerosis. 127, 195-203.). Targeted deletion of the gene for lumican in mice, results in corneal opacity as well as fragile skin (Saika et al. 2000; Chakravarti et al. (1998) The Journal of Cell Biology 141, 1277-1286; Chakravarti et al. (2000) Investigative Ophthalmology & Visual Science 41, 33656-3373).

Lumican is composed of a 38 kDa core protein to which may be attached to asparagine residues up to 3 keratan sulfate GAG side chains and/or 2 to 3 oligosaccharides not containing keratan sulfate (Dunlevy et al. (1998) The Journal of Biological Chemistry 273, 9615-9621; Nilsson et al. (1983) The Journal of Biological Chemistry 258, 6056-6063; Midura & Hascall (1989) The Journal of Biological Chemistry 264, 1423-1430). The keratan sulfate chains are composed of linear repeating disaccharide units of N-acetylglucsoamine and galactose (N-acetyllactosamine), and are attached to the protein via an N-glycosidic linkage to N-acetylglucsoamine within a mannose-containing linker oligosaccharide (Nilsson et al. (1983); Funderburgh et al. (2000) Glycobiology 10, 951-958.). The core protein is also known to be sulfated on tyrosine residues (Onnerfjord et al. (2004) The Journal of Biological Chemistry 279, 26-33). The isolated core protein, free of carbohydrate modifications ("lumican-P38"), is often observed in cultured cells, but typically not in human tissues (Qin et al. (2001) J. Pathol. 195, 604-608). In tissue, lumican may be present as a 55 kDa low-sulfated glycoprotein ("lumican-P55"), or as a keratan sulfate proteoglycan ("lumican proteoglycan"), with an apparent mass ranging from 60-100 kDa (Sztrolovics et al. (1999) Spine 1765-1771; Funderburgh et al. (1991); Dolhnikoff et al. (1998) Am J. Respir. Cell Mol. Biol. 19, 582-587; Qin et al. (2001)). Lumican-P55 appears to be relatively widely expressed, being present in most normal tissues, including arterial adventitia (Funderburgh et al. (1991)). In contrast, lumican proteoglycan appears to have a more restricted distribution (e.g., present primarily in normal cornea and cartilage) and have biological effects that are distinct from those of lumican-P55.

There is evidence that some lumicans may play a role in atherosclerosis. One study showed that a keratan sulfate proteoglycan was upregulated in arterial lesions of cholesterol-fed pigeons, compared with normal arteries (Robbins et al. (1992) Arteriosclerosis and thrombosis 12, 83-91). A large-scale gene expression profiling revealed lumican to be one of 55 gene-products upregulated in human atherosclerotic coronary arteries compared with normal coronary arteries (Archacki et al. (2003) Physiology Genomics 15, 64-74). The lumican gene is also expressed in the aortas of mice fed a high-fat diet (Tabibiazar et al. (2005) Arteriosclerosis Thrombosis and Vascular Biology 25, 302-308). By immunohistochemistry, in normal human coronary arteries, lumican is present in the adventitia but absent from the intima (Onda et al. (2002) Expirimental and Molecular Biology 72, 142-149). This adventitial lumican represents the widely expressed lumican-P55, which has been purified from normal bovine aorta (Funderburgh et al. (1991)). However, human intimal hyperplasia and atherosclerotic lesions both demonstrate immunoreactivity for lumican within the intima (Onda et al. "(2002)).

A further understanding of the proteoglycan composition in the thickened intima may lead to the development of therapeutics and diagnostics that target the progression of intimal hyperplasia to atherosclerosis.

SUMMARY OF THE INVENTION

The present invention is based, at least in part, on the determination that the lumican within the human hyperplasia and/or atherosclerotic intima is lumican proteoglycan.

The present invention is also based, at least in part, on the determination that a significant difference between the intimal hyperplasia within atherosclerosis prone arteries and atherosclerosis-resistant arteries is the increased composition of lumican proteoglycan in the atherosclerosis-prone arteries. Accordingly, the present invention provides therapeutic methods which reduce the accumulation of lumican proteoglycan in atherosclerosis-prone arteries.

In one aspect, the present invention provides a method of reducing atheroma formation in a subject, comprising reducing accumulation of lumican proteoglycan in the intima of an artery, thereby reducing atheroma formation in the subject. In a specific embodiment, atheroma formation is inhibited.

In another aspect, the present invention provides a method of treating an atherosclerotic lesion in a subject, comprising reducing the amount of lumican proteoglycan in the lesion, thereby treating the atherosclerotic lesion in the subject. In a specific embodiment, the atherosclerotic lesion is eradicated.

In one embodiment, accumulation of lumican proteoglycan is reduced by administering an agent that is an inhibitor of lumican proteoglycan synthesis to the subject. In specific embodiments, the agent inhibits the synthesis of the lumican proteoglycan core protein or lumican proteoglycan keratan sulfate side chains. The agent can be administered directly to a blood vessel of the subject.

In another embodiment, the agent inhibits an enzyme including but not limited to a sulfotransferase, beta1, 4 galactosyltransferase and beta1, 3-N-acetylglucosaminyltransferase. The sulfotransferase can be, for example, N-acetylglucosamine 6-O-sulfotransferase or keratan sulfate galactose-sulfotransferase.

In yet another aspect, the invention provides a method of identifying a subject having, or at risk of having, atherosclerosis, comprising detecting an increased amount of lumican proteoglycan in a biological sample obtained from the subject, wherein the amount of lumican proteoglycan is increased relative to a control, thereby identifying a subject having, or at risk of having, atherosclerosis.

In yet another aspect, the invention provides a method of identifying a subject having, or at risk of having, atherosclerosis, comprising detecting in an artery of the subject an increased amount of lumican proteoglycan in the intimal layer, thereby identifying a subject having, or at risk of having, atherosclerosis.

In one embodiment, the amount of lumican proteoglycan is determined by measuring the amount of core protein or keratan sulfate side chains in the sample.

In another embodiment, the biological sample comprises serum.

In yet another aspect, the invention provides a kit for treating an atherosclerotic lesion comprising an agent that reduces lumican proteoglycan in the lesion and instructions for use thereof. The agent contained in the kit can be an inhibitor of lumican proteoglycan synthesis.

In yet another aspect, the invention provides a packaged pharmaceutical comprising:

a) an agent that reduces the amount of lumican proteoglycan in an atherosclerotic lesion comprising, and
b) instructions for using said agent to treat said atherosclerotic lesion.

The agent contained in the packaged pharmaceutical can be an inhibitor of lumican proteoglycan synthesis.

Other aspects of the invention are described in or are obvious from the following disclosure, and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 6 illustrates enhanced Mass Spectral Signal Intensity for Lumican in the Atherosclerosis-Prone Internal Carotid Artery determined through mass spec analysis. Mass spectral signal intensities for selected peptides from (A) versican, (B) biglycan, (C) fibromodulin, and (D) lumican from the two arterial sites were compared. The signal intensities were normalized to the total amount of intimal protein extracted. Horizontal bars indicate the mean values. The y-axes are arbitrary units in a linear scale starting at zero.

DETAILED DESCRIPTION OF THE INVENTION

Figure 1A:
FIG. 1 shows results of histological staining of the intimal hyperplasia in the distal ulnar artery of the hand. (A) shows Hematoxylin and Eosin stain. (B) shows elastic stain illustrating fragmented internal elastic lamina. Arrows indicate the level of the internal elastic lamina.

The invention relates to methods of reducing formation of atheromas and methods of treating atherosclerotic lesions and/or atherosclerosis by reducing the amount of lumican proteglycan in the intima or an artery or in the lesion. The invention also relates to methods of identifying subjects having or at risk of having atherosclerosis comprising detecting an increased amount of lumican proteoglycan in a biological sample.

I. Definitions

As used herein, the terms "atherosclerotic lesion," "atherosclerotic plaque" and "atheroma" are used interchangeably and refer to an area of thickening in the wall of an artery caused by white blood cells (monocytes) migrating from the bloodstream into the wall of the artery. In the artery, the monocytes are transformed into cells that accumulate fatty materials (foam cells). Eventually, the fat-laden monocytes accumulate, leading to a patchy thickening in the inner lining of the artery. An atherosclerotic lesion is clinically defined as the presence of numerous foam cells or a necrotic/lipid core, including classic type II lesions and above (Stary et al., 1994 Circulation 89:2462) in the wall of an artery. Methods of detecting atherosclerotic lesions are well known in the art (Cury et al., (2006) Investigative Radiology, 41(2):112). "Atheroma formation" refers to the formation of "atheromas" as defined herein.

As used herein, "reducing" as it refers to atheroma or atherosclerotic lesion formation, means to decrease the size of an atheroma or atherosclerotic lesion by at least about 1.1-fold or decrease the size of an atheroma or atherosclerotic lesion by at least about 10% as compared to the size measured prior to reducing accumulation of lumican proteoglycan in the intima of an artery as defined herein. "Reducing" as it refers to atheroma or atherosclerotic lesion formation also means to decrease the number of atheromas or atherosclerotic lesions by at least about 1.1-fold or decrease the number of atheromas or atherosclerotic lesions by at least about 10% as compared to the number measured prior to reducing accumulation of lumican proteoglycan in the intima of an artery as defined herein. Reducing atheroma or atherosclerotic lesion formation also means to decrease atheroma or atherosclerotic lesion formation (both size and number) to a basal level, as defined herein, or to a level exhibited in a subject that does not have atherosclerosis.

As used herein, "intima" or "tunica intima" refers to the innermost layer of an artery. The "intima" is made up of one layer of endothelial cells and is supported by an internal elastic lamina. The endothelial cells of the intima are in direct contact with the blood flow. An "intimal hyperplasia" is clinically defined as an intima greater than 0.03 mm thick with or without isolated/focal foam cells, which are essentially lipid rich macrophage cells. Vessels with an intimal thickness of less than 0.03 mm are considered normal. Morphometric analyses can be performed using a microscope (e.g., Nikon Eclipse E600 equipped with a Hitachi HV-C20 3-CCD digital camera with computer interface and IPLab Spectrum software (Signal Analytics, Vienna, Va.)). Macrophages are identified as cells staining positively for macrophage marker CD68. The number of macrophages present is typically determined by visual inspection and manual counting. The number of macrophages present is then divided by the intimal area (in square millimeters) determined by morphometric analysis.

As used herein, "lumican proteoglycan" refers to a member of the small leucine-rich family of proteoglycans. "Lumican proteoglycan" includes the lumican proteoglycan core protein and the lumican proteoglycan keratan side chains, defined herein. Lumican proteoglycan is upregulated in atherosclerotic vessels as compared to normal vessels.

The "lumican proteoglycan core protein" is a 38 kDa core protein to which may be attached to asparagines residues up to three keratan sulfate GAG side chains and/or two to three oligosaccharides not containing keratin sulfate. This protein is described in GenBank, under accession number NM_002345, the contents of which are expressly incorporated herein by reference.

"Lumican proteoglycan keratan sulfate side chains" refers to keratan sulfate GAG side chains that may be attached to asparagine residues of the lumican proteoglycan core protein. The keratan side chains are composed of linear repeating disaccharide units of N-acetylglucosamine and galactose (N-acetyllactosamine) and are attached to the protein via an N-glycosidic linkage to N-acetylglucosamine within a mannose-containing linker oligosaccharide.

As used herein, "subject" refers to a mammal.

As used herein, "mammal" refers to any mammal including but not limited to human, mouse, rat, sheep, monkey, goat, rabbit, hamster, horse, cow or pig.

A "non-human mammal", as used herein, refers to any mammal that is not a human.

As used herein "accumulation of lumican proteoglycan" refers to an increase in the amount of lumican proteogylcan that is at least about 2-fold (for example, about 2, 3, 4, 5, 10, 15, 20, 25, 30, 35, 40, 45, 50, 55, 60, 65, 70, 75, 80, 85, 90, 95, 100, 1000 or more) or at least about 2% (for example, about 2, 3, 4, 5, 10, 15, 20, 25, 30, 35, 40, 45, 50, 55, 60, 65, 70, 75, 80, 85, 90, 95, 99, or 100%) as compared to the amount of lumican proteoglycan in a basal state or in a subject that does not have atheroma or atherosclerotic lesion formation and/or atherosclerosis.

As used herein, "reducing" or "decreasing" as it refers to reducing lumican proteoglycan, means to decrease the detectable amount of lumican proteoglycan, for example, in the intima of an artery, by at least about 1.1-fold or by at least about 10% as compared to the amount measured prior to reducing accumulation of lumican proteoglycan in the intima of an artery as defined herein. The amount of lumican proteoglycan includes the amount of mRNA encoding lumican proteoglycan and lumican proteoglycan protein.

As used herein, "inhibits" as it refers to atheroma or atherosclerotic lesion formation means decreasing the number of atheromas or atherosclerotic lesions formed by at least about 2-fold (for example about 2, 3, 4, 5, 10, 15, 20, 25, 30, 35, 40, 45, 50, 55, 60, 65, 70, 75, 80, 85, 90, 95, 100, 1000 or more) or at least about 2% (for example, about 2, 3, 4, 5, 10, 15, 20, 25, 30, 35, 40, 45, 50, 55, 60, 65, 70, 75, 80, 85, 90, 95, 99, or 100%), as compared to atheroma or atherosclerotic lesion formation in a subject wherein lumican proteoglycan has not been reduced in the intima of an artery. As used herein, "inhibits" as it refers to atheroma or atherosclerotic lesion formation also means decreasing the size of atheromas or atherosclerotic lesions formed by at least about 2-fold (for example 2, 3, 4, 5, 10, 15, 20, 25, 30, 35, 40, 45, 50, 55, 60, 65, 70, 75, 80, 85, 90, 95, 100, 1000 or more) or at least about 2% (for example, 2, 3, 4, 5, 10, 15, 20, 25, 30, 35, 40, 45, 50, 55, 60, 65, 70, 75, 80, 85, 90, 95, 99, or 100%), as compared to the size of atheromas or atherosclerotic lesions formed in a subject wherein lumican proteoglycan has not been reduced in the intima of an artery. Inhibition of atheroma or atherosclerotic lesion formation includes preventing formation altogether.

As used herein, "inhibits the synthesis" means decreasing or inhibiting protein or mRNA synthesis by at least about 2-fold (for example 2, 3, 4, 5, 10, 15, 20, 25, 30, 35, 40, 45, 50, 55, 60, 65, 70, 75, 80, 85, 90, 95, 100, 1000 or more) or at least about 2% (for example, 2, 3, 4, 5, 10, 15, 20, 25, 30, 35, 40, 45, 50, 55, 60, 65, 70, 75, 80, 85, 90, 95, 99, or 100%), as compared to the amount of synthesis, for example, in a subject that has not been treated with an agent that is an inhibitor of synthesis.

As used herein, "inhibits an enzyme" means decreasing or inhibiting the amount of enzyme activity by at least about 2-fold (for example about 2, 3, 4, 5, 10, 15, 20, 25, 30, 35, 40, 45, 50, 55, 60, 65, 70, 75, 80, 85, 90, 95, 100, 1000 or more) or at least about 2% (for example, about 2, 3, 4, 5, 10, 15, 20, 25, 30, 35, 40, 45, 50, 55, 60, 65, 70, 75, 80, 85, 90, 95, 99, or 100%), as compared to the amount of enzyme activity, for example, in a subject that has not been treated with an inhibitor on enzyme activity.

As used herein, an "inhibitor" refers to an agent, such as an antibody, protein, small organic molecule or targeted nucleic acid (e.g., siRNA), that decreases or inhibits, as defined herein, for example, mRNA or protein synthesis, protein accumulation, atheroma formation and atherosclerotic lesion formation.

As used herein, "treating" an atherosclerotic lesion, an atheroma or atherosclerosis refers to decreasing the size or number of atherosclerotic lesions or preventing the formation of atherosclerotic lesions, or delaying the onset of formation of atherosclerotic lesions. By "treating" is also meant restoring the subject to the basal state as defined herein, to prevent atherosclerosis or the formation of an atherosclerotic lesion or atheroma in a subject at risk thereof, or restoring the subject's artery to the basal state. Alternatively, "treating" means arresting or otherwise ameliorating the signs and symptoms of atherosclerosis, including but not limited to the presence of foam cells, the presence of a necrotic or lipid core, which is the acellular center of an atherosclerotic plaque that contains debris from dead cells, lipids, and cholesterol clefts, thickening of an artery, and a decrease in the elasticity of an artery, cramps, and chest pain.

As used herein, "obtaining" as in "obtaining the agent" includes synthesizing, purchasing or otherwise acquiring the agent.

As used herein, "diagnosis" or "identifying a subject having" refers to a process of determining if an individual is afflicted with a disease or ailment, for example atherosclerosis. Atherosclerosis is diagnosed for example by detecting either the presence of foam cells or the presence of a necrotic or lipid core in an artery as well as other signs and symptoms including dyspnea, shortness of breath, activity intolerance, and myocardial ischemia.

As used herein "susceptible to" or "at risk of having" means having a propensity for developing, for example is expected to develop atherosclerosis. It is contemplated that a subject is at risk of developing atherosclerosis based upon at least any one of a particular pathological process including but not limited to shortness of breath, an occluded or stenotic vessel or evidence of tissue ischemia. Accordingly, the clinical diagnosis of atherosclerosis is typically based on evidence of tissue ischemia, such as by an EKG or clinical history and also by radiologic imaging of an occluded or stenotic vessel usually by angiography or ultrasound. Indicators of increased susceptibility to atherosclerosis are age over 40, male gender, high blood pressure, elevated cholesterol, elevated C-reactive protein, presence of diabetes, or positive family history.

As used herein, "reducing" as it refers to accumulation of lumican proteoglycan means to decrease by at least about 2-fold (for example about 2, 3, 4, 5, 10, 15, 20, 25, 30, 35, 40, 45, 50, 55, 60, 65, 70, 75, 80, 85, 90, 95, 100, 1000 or more) or at least about 2% (for example, about 2, 3, 4, 5, 10, 15, 20, 25, 30, 35, 40, 45, 50, 55, 60, 65, 70, 75, 80, 85, 90, 95, 99, or 100%) the amount of lumican proteoglycan, for example in the intima of an artery or atherosclerotic lesion, as compared to the amount measured prior to, for example, providing an agent that is an inhibitor of lumican proteoglycan synthesis, as defined herein.

As used herein, a "basal state" refers to the artery of an individual who is not susceptible to atheroma or atherosclerotic lesion formation or atherosclerosis and has no detectable atheromas or atherosclerotic lesions or symptoms of atherosclerosis. Preferably, a basal state refers to no detectable atheromas or atherosclerotic lesions, no detectable atheromas or atherosclerotic lesions.

As used herein "eradicate" or "eliminate" means decrease to a amount that is undetectable.

"Measuring" means detecting or measuring, for example, atheroma formation, accumulation of lumican proteoglycan, synthesis of lumican proteoglycan, including synthesis of lumican proteoglycan core protein and lumican proteoglycan keratin sulfate side chains, or enzyme activity, according to the methods described herein. "Measuring" according to the invention is performed in vitro or in vivo, for example in an artery, in an atherosclerotic lesion, in serum or in blood or other biological sample, tissue or organ.

"Measuring" also means detecting a change that is either an increase or decrease in the amount of atheroma or atherosclerotic lesion formation, lumican proteoglycan amounts or lumican proteoglycan synthesis, according to the methods described herein. "Measuring" is performed in a subject that has atheroma or atherosclerotic lesion formation and/or is diagnosed with atherosclerosis or in a biological sample derived from the subject, prior to and following reduction of lumican proteoglycan accumulation in the intima of an artery. The amount of atheroma or atherosclerotic lesion formation in the subject is compared to the amount of atheroma or atherosclerotic lesion formation in the same subject prior to reducing lumican proteoglycan accumulation in the intima of the artery, or to the amount in the basal state or in a subject that is not diagnosed with atherosclerosis.

A method of "administration" useful according to the invention includes but is not limited to administration directly to a blood vessel, including artery, vein or capillary, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced agent or may, instead, comprise cells that produce and secrete the therapeutic agent or topical application. Additional methods of administration are provided hereinbelow in the section entitled "Dosage and Administration."

As used herein, the term "biological sample" or "sample" refers to a whole organism or a subset of its tissues, cells or component parts (e.g. blood vessel, including artery, vein and capillary, body fluids, including but not limited to blood, serum, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

II. Atherosclerosis

Atherosclerosis is the buildup of plaque on the inside walls of arteries. Plaque is made up of low density lipoprotein (LDL), macrophages, smooth muscle cells, platelets, and other substances. It may narrow the lumen of a blood vessel and restrict blood flow. Plaque rupture can induce the formation of thrombus (blood clot) and block blood flow. This will result in ischemic stroke or heart attack.

The first stage in the development of atherosclerosis is the formation of foam cells (macrophages with ingested oxidized LDL). The process begins with the accumulation of LDL in the intima, which lies just below the endothelium (the monolayer of cells lining the arterial wall). Trapped LDL could be oxidized, triggering recruitment of monocytes into the intima. Several adhesion molecules are involved, including vascular-cell adhesion molecule (VCAM), integrin, selectin, and others. After entering the intima, monocytes differentiate into macrophages and ingest oxidized LDL.

As atherosclerosis progresses, T lymphocytes, platelets and smooth muscle cells also join foam cells, expanding the plaque size. This involves cytokines to activate T lymphocytes and growth factors to promote proliferation of smooth muscle cells. Platelets can also release cytokines and growth factors to enhance migration and proliferation of smooth muscle cells. During this stage, a fibrous cap is formed to separate the plaque from the lumen.

Atherosclerosis can affect the arteries of the brain, heart, kidneys, other vital organs, and the arms and legs. When atherosclerosis develops in the arteries that supply the brain (carotid arteries), a stroke may occur; when it develops in the arteries that supply the heart (coronary arteries), a heart attack may occur.

Arteries affected with atherosclerosis lose their elasticity, and as the atheromas grow, the arteries narrow. With time, the atheromas collect calcium deposits, may become brittle, and may rupture. Blood may then enter a ruptured atheroma, making it larger, so that it narrows the artery even more. A ruptured atheroma also may spill its fatty contents and trigger the formation of a blood clot (thrombus). Thrombosis (formation of thrombus) arises from plaque rupture. Macrophages may release metalloproteinases and other proteolytic enzymes to degrade fibrous cap, making it susceptible to rupture. Plaque rupture activates platelets, leading to formation of blood clots at the site of lesion. The clot may further narrow or even occlude the artery, or it may detach and float downstream where it causes an occlusion (embolism).

Usually, atherosclerosis doesn't produce symptoms until it severely narrows the artery, or until it causes an obstruction. Symptoms depend on where the atherosclerosis develops; thus, they may reflect problems in the heart, the brain, the legs or almost anywhere in the body. As atherosclerosis severely narrows an artery, the areas of the body it serves may not receive enough blood, which carries oxygen to the tissues. The first symptom of a narrowing artery may be pain or cramps at times when the blood flow can't keep up with the body's demand for oxygen. For instance, during exercise, a person may feel chest pain (angina) because of a lack of oxygen to the heart, or while walking, a person may feel leg cramps (intermittent claudication) because of a lack of oxygen to the legs. Typically, these symptoms develop gradually as the atheroma slowly narrows the artery. However, when an obstruction occurs suddenly, for example, when a blood clot lodges in an artery, the symptoms come on suddenly.

The risk of developing atherosclerosis increases with high blood pressure, high blood cholesterol levels, cigarette smoking, diabetes, obesity, a lack of exercise, and advancing age. Having a close relative who developed atherosclerosis at an early age also puts a person at risk. Men have a higher risk than women, though after menopause, the risk increase in women and eventually equals that in men.

People with the inherited disease homocystinuria develop extensive atheroma formation, particularly at a young age. The disease affects many arteries but doesn't primarily affect the coronary arteries, which supply the heart. In contrast, in the inherited disease familial hypercholesterolemia, extremely high levels of blood cholesterol cause atheromas to form in the coronary arteries much more than in other arteries.

III. Lumican Proteoglycan

Lumican proteoglycan, including the core protein and proteoglycan keratan sulfate side chains, are reviewed in detail hereinabove.

Enzymes involved in the synthesis of lumican proteoglycan include but are not limited to sulfotransferase, beta1, 4 galactosyltransferase and beta1, 3-N-acetylglucosaminyl-transferase.

A sulfotransferase useful according to the invention includes but is not limited to N-acetylglucosamine 6-O-sulfotransferase or keratan sulfate galactose-sulfotransferase, which are known in the art and described, for example in Funderburgh J. L. (2002) *IUBMB Life* 54:187-194, the contents of which are expressly incorporated herein by reference.

IV. Detection of Lumican Proteoglycan

Lumican proteoglycan protein, including lumican proteoglycan core protein and proteoglycan keratan sulfate side chains, and mRNA encoding lumican proteoglycan protein, including lumican proteoglycan core protein and proteoglycan keratan sulfate side chains is detected or measured by methods known in the art.

The level of lumican proteoglycan protein can be detected or measured by the methods of immunoprecipitation, immunohistochemistry, ELISA and FACs analysis as described in the art (described in Ausubel et al., 1995, Short Protocols in Molecular Biology, 3rd Edition, John Wiley & Sons; Sambrook et al., 1989, Molecular Cloning. A Laboratory Manual., 2nd Edition, Cold Spring Harbor Laboratory Press, Cold Spring Harbor, N.Y.).

The level of lumican proteoglycan mRNA is measured by methods known in the art including but not limited to RT-PCR, northern blot analysis, RNase protection analysis, primer extension, in situ hybridization (described in Ausubel et al., 1995, Short Protocols in Molecular Biology, 3rd Edition, John Wiley & Sons; Sambrook et al., 1989, Molecular Cloning. A Laboratory Manual., 2nd Edition, Cold Spring Harbor Laboratory Press, Cold Spring Harbor, N.Y.).

The invention provides for detecting lumican proteoglycan protein and mRNA in vitro and in vivo, for example, in the artery, in atherosclerotic lesions, in blood, plasma and in serum. Comparison of the amounts of lumican proteoglycan in a diseased subject, determined in vivo or in biological samples, to amounts known to be present in healthy subjects will provide a measurement that is indicative of atherosclerosis in the subject. Biological samples, including arterial specimens, blood, plasma and serum, are isolated according to methods known in the art and described herein below.

Where the amount of lumican proteoglycan is measured in a biological sample, such as serum, obtained from a subject, measurement of at least about 200 ng/mL of lumican proteoglycan in the sample would indicate the onset of atherosclerotic disease. Preferably, measurement is performed by methods of enzyme-linked immunosorbant assay (ELISA) known in the art.

In specific embodiments, arterial specimens would be assayed. Arterial specimens can be isolated according to any method known in the art. For example, a representative cross-section of the segment is fixed in 10% buffered formalin for 16 hours, processed with paraffin embedding, and used to generate hematoxylin-and-eosin-stained histological slides. The remainder of the tissue is stored at −80° C. for proteomic analysis.

An exemplary protocol for the isolation and detection of proteogylcans from arterial samples is as follows. Arteries are rinsed in cold phosphate-buffered saline (67 mM phosphate and 150 mM NaCl, pH 7.0) and opened longitudinally. The thickened intima is carefully removed and finely diced with a razor blade. The accuracy of the intimal dissection is verified by histological analysis. To account for the larger size of the internal carotid arteries, both segments of internal thoracic artery from a given patient are processed together. The intimal tissue fragments are extracted with 8 ml of buffer A (50 mM Tris, pH 7.4, containing 7 M urea, 0.1 M NaCl, complete protease inhibitor mixture (Roche Applied Science; 1 tablet/50 ml), and 5 mM dithiothreitol) for 48 hours at 4° C. Afterward, the samples are centrifuged at 3000×g for 5 min to remove the tissue fragments. Aliquots (0.1 ml) of the supernatant are retained for total protein determination, using the Bradford microassay (Bio-Rad).

To the remaining supernatant is added 50 μl of hydrated Macro-Prep High Q Support strong anion exchange resin (Bio-Rad). The mixture is incubated at 4° C. with rocking for 20 minutes. The resin and bound proteoglycans are sedimented by centrifugationfor 5 min at 3000×g. The resin is placed in a spin column and washed sequentially with the following buffers by application of 0.5 ml of the buffer followed by centrifugation for 5 min at 3000×g: 1 wash with buffer A, followed by 2 washes with buffer B (buffer A with an additional 0.1 M NaCl), followed by three washes with buffer C (6 M urea, 0.2 M NaCl, and 50 mM sodium acetate, pH 3.7), and finally two washes with buffer B. The proteoglycans are then eluted from the resin by the application of 100 μl of 50 mM Tris, pH 7.4, containing 6 M urea and 1 M NaCl, followed by centrifugation for 5 minutes at 3000×g. Aliquots of the purified proteoglycans are electrophoresed into a short (1 cm) 4% SDS-PAGE gel, which is subsequently fixed with 40% methanol, 10% acetic acid, and then stained with colloidal Coomassie (Bio-Rad).

Gel portions containing the proteoglycans are subjected to tryptic in-gel digestion and the tryptic peptides are extracted and separated by nanoscale reverse-phase high performance liquid chromatography followed by electrospray ionization as described in detail previously (Stone et al., Biochemistry 42:1301). Tandem mass spectra are obtained on a Finnigan LTQ linear ion-trap mass spectrometer (Thermo Electron Corporation). Every MS/MS spectrum obtained can be used to search the human NCI database (130,741 protein entries when searched) using Sequest version 27.9. The database is searched using no enzyme specificity and a precursor ion mass accuracy of ±1 Da, allowing for the differential modification of Met (+16 Da, oxidation) and Cys (+71 Da, monoacrylamide) and for up to three missed cleavagesites. After the initial search, non-tryptic peptide matches are discarded. The remaining matches are manually inspected for quality. Those matches typically considered true matches had Cn scores of at least 0.1 and XCorr values of 2.0 or greater for +1 and +2 charged peptides and 3.5 or greater for +3 charged peptides. A particular proteoglycan is considered to be present only if two or more such high quality peptides are identified in at least one of the intimal preparations.

Aliquots of the purified proteoglycans are subjected to SDS-PAGE on 4-20% gradient polyacrylamide gels (Bio-Rad) and electrophoresed at 200 volts. Gels are blotted onto PVDF membrane. Membranes are probed with primary antibodies to fibromodulin (1:200 dilution), biglycan (1:1000 dilution), or lumican (1:1000 dilution). Goat polyclonal antibodies to fibromodulin are obtained from Santa Cruz Biotechnology. Rabbit polyclonal antibodies to lumican and biglycan are prepared as described previously (Grover et al., 1995 J. Biol. Chem. 270:21942; Roughley et al., 1996 Biochem J. 318:779). Blots are then treated with the appropriate peroxidase-conjugated secondary antibody: donkey anti-goat (Jackson) at 1:5000 dilution or donkey anti-rabbit (Santa Cruz) at 1:2000 dilution. Blots are imaged using ECL-plus chemiluminescence detection kits (Amersham Biosciences) and film which was developed on an X-Omat processor. Bands are quantitated using a GS-800 laser densitometer (Bio-Rad). To compensate for the variation in the amount of intimal tissue removed from the different arterial segments, all chemiluminescence values are normalized to the total amount of protein extracted from the intimal portions. Statistical analyses (Student's t tests) are performed using Graph-Pad software.

V. Methods of Treatment

The invention provides for methods of reducing atheromas, and treating atherosclerotic lesions and atherosclerosis comprising reducing accumulation of lumican proteoglycan, for example, in the intima of an artery.

Accumulation of lumican proteogylcan is reduced, for example, by an agent that inhibits synthesis of lumican proteoglycan, including lumican proteoglycan core protein and proteoglycan keratan sulfate side chain synthesis or an agent that inhibits an enzyme including but not limited to sulfotransferase, betal, 4 galactosyltransferase and betal, 3-N-acetylglucosaminyltransferase, as defined herein.

Inhibitors of the aforementioned enzymes are known in the art. Triclosan, for example, is an antibacterial inhibitor of sulfotransferases known in the art. Alkylamines are also known to inhibit sulfotransferases. 2,6-Dichloro-4-nitrophenol has also been reported to inhibit the activity of sulfotransferase. Antibodies that specifically interfere with the activity of these enzymes can also be generated according to methods known in the art.

An "agent" as used herein, is any compound that reduces accumulation of lumican proteoglycan according to the invention.

An agent is tested in a concentration range that depends upon the molecular weight of the drug and the type of assay. For example, 1 pg-100 µg/ml, about 100 pg-10 ng/ml; 10 ng-100 µg/ml, or 100 ng-10 µg/ml.

Candidate agents from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (N.C.), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, and preferably small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

As used herein, "treating" refers to preventing the onset of formation of atheromas or atherosclerotic lesions, or atherosclerosis, and/or reducing, delaying, or eliminating atheromas, atherosclerotic lesions or atherosclerosis symptoms such as the presence of more than one foam cells and or a necrotic or lipid core, thickening of the artery. By "treating" is meant restoring the subject to the basal state as defined herein or to prevent atheroma or atherosclerotic lesion formation or atherosclerosis in a subject at risk thereof, or restoring the subject's artery to the basal state. Alternatively, "treating" means arresting or otherwise ameliorating symptoms of atherosclerosis as defined herein.

As used herein delay means to retard or hinder the appearance of one of more symptoms of atherosclerosis or formation of atheromas or atherosclerotic lesions as defined herein. A "delay" according to the invention can be at least about 2 hours or more, for example, about 2, 6, 12, 24, 36, 48, 60, 72 hours or 3 days or more, for example, about 3, 4, 5, 10, 15, 20, 25, 30 or more days.

According to the method of the invention, atheromas, atherosclerotic lesions and atherosclerosis are treated, as defined herein, by administration of an agent that reduces accumulation of lumican proteoglycan, for example in the intima of an artery or in an atherosclerotic lesion.

According to the methods of the invention, the efficacy of disease treatment according to the invention is assessed by monitoring changes in the disease state in subjects receiving an agent that reduces accumulation of lumican proteoglycan, for example in the intima of an artery or in an atherosclerotic lesion and comparing them to the progression or persistence of disease in control subjects who are treated with placebos (i.e. a pharmaceutically-acceptable carrier without the therapeutic agent).

VI. Dosage and Mode of Administration

By way of example, a patient suffering from or susceptible to atheroma or atherosclerotic lesion formation or atherosclerosis as described herein can be treated as follows. An agent that reduces accumulation of lumican proteoglycan, for example in the intima of an artery or an atherosclerotic lesion can be administered to the patient, preferably in a biologically compatible solution or a pharmaceutically acceptable delivery vehicle, by ingestion, injection, inhalation, or any number of other methods. The dosages administered will vary from patient to patient; a "therapeutically effective dose" can be determined, for example, by monitoring the level of capillary permeability or extracellular fluid volume.

In the treatment of atheromas, atherosclerotic lesions or atherosclerosis, a therapeutically effective dosage regimen should be used. By "therapeutically effective", one refers to a treatment regimen sufficient to restore the subject to the basal state, as defined herein, at the cellular or tissue site of manifestation or to prevent atheroma or atherosclerotic lesion formation or atherosclerosis in an individual at risk thereof or restore the subject's artery to the basal state. Alternatively, a "therapeutically effective regimen" may be sufficient to arrest or otherwise ameliorate symptoms of atherosclerosis. Generally, in the treatment of atheromas, atherosclerotic lesions and atherosclerosis, an effective dosage regimen involves providing the medication over a period of time to achieve noticeable therapeutic effects.

Generally, a therapeutic composition of the invention will be administered in a single dose in the range of from about 1 fg to about 1 g per kg body weight, preferably about 1 ug to about 1 mg per kg body weight. This dosage may be repeated daily, weekly, monthly, yearly, or as considered appropriate by the treating physician.

It is contemplated that global administration of a therapeutic composition to an animal is not needed in order to achieve a highly localized effect. Localized administration of a therapeutic composition according to the invention is preferably by injection, catheter or by means of a drip device, drug pump or drug-saturated solid matrix from which the composition can diffuse implanted at the target site. When a tissue that is the target of treatment according to the invention is on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Compositions comprising a therapeutic composition which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

Note that in some cases, the surface in question is internal; in such a case, topical application would comprise taking the therapeutic composition via an oral route, whether in liquid, gel or solid form.

Systemic administration of a therapeutic composition according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device. Note that injection may be performed either by conventional means (i.e. using a hypodermic needle) or by hypospray (see Clarke and Woodland, 1975, *Rheumatol. Rehabil.*, 14: 47-49).

Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

A therapeutic composition of use in the invention can be given in a single- or multiple dose. A multiple dose schedule is one in which a primary course of administration can include 1-10 separate doses, followed by other doses given at subsequent time intervals required to maintain and or reinforce the level of the therapeutic agent. Such intervals are dependent on the continued need of the recipient for the therapeutic agent, and/or the half-life of a therapeutic agent. The efficacy of administration may be assayed by monitoring the reduction in the levels of a symptom indicative or associated with atherosclerosis which it is designed to inhibit. The assays can be performed as described herein or according to methods known to one skilled in the art.

A therapeutically effective regimen may be sufficient to arrest or otherwise ameliorate symptoms of a disease. An effective dosage regimen involves providing the regulatory drug over a period of time to achieve noticeable therapeutic effects wherein symptoms are reduced to a clinically acceptable standard or ameliorated. The symptoms are specific for the disease in question. For example, when the disease is associated with tumor formation, the claimed invention is successful when tumor growth is arrested, or tumor mass is decreased by at least 50% and preferably 75%.

VII. Pharmaceutical Compositions

The invention provides for compositions comprising an agent or compound according to the invention, for example an agent that reduces accumulation of lumican proteoglycan, for example in the intima of an artery or an atherosclerotic lesion, admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the subject.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc . . . Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a Ph range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

VIII. Kits or Pharmaceutical Systems

The present compositions may be assembled into kits or pharmaceutical systems for use in reduction of atheromas, treatment of atherosclerotic lesions or treatment of atherosclerosis. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the agents of the invention, for example an agent that reduces accumulation of lumican proteoglycan for reducing atheroma formation and/or treating atherosclerotic lesions and atherosclerosis.

Having now generally described the invention, the same will be more readily understood through reference to the following Examples which are provided by way of illustration, and are not intended to be limiting of the present invention, unless specified.

The following examples are put forth for illustrative purposes only and are not intended to limit the scope of what the inventors regard as their invention.

EXAMPLES

Example 1

Distal Ulnar Artery is an Atherosclerosis-Resistant Artery

Figure 1B:
Figures 2A, 2B:
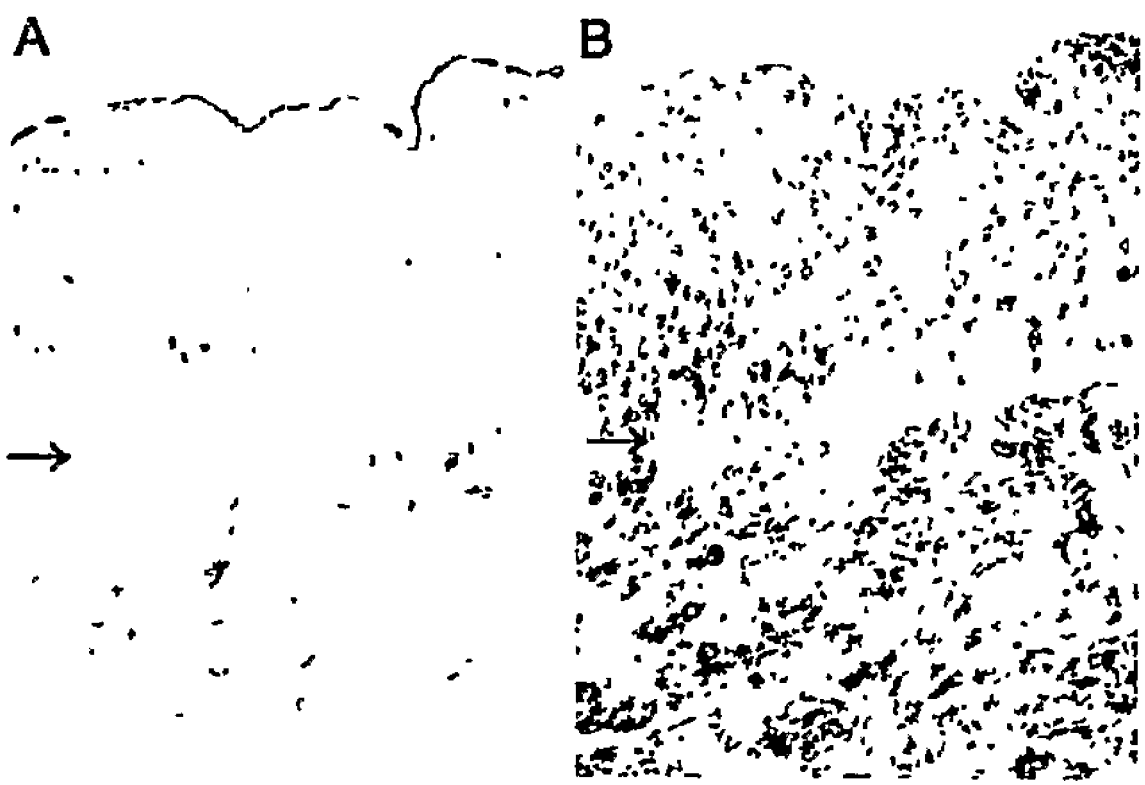
FIG. 2 shows immunohistochemical analysis of intimal hyperplasia in the distal ulnar artery. (A) shows immunohistochemistry for CD34, with reactivity of the endothelium. (B) shows immunohistochemistry for alpha smooth muscle actin, with diffuse reactivity of the medial and intimal smooth muscle cells. Arrows indicate the level of the internal elastic lamnina.

The distal ulnar artery has been shown to be an atherosclerosis-resistant artery (Stone (2004) *Cardiovascular Pathology* 13, 20-25). However, the superficial ulnar artery in the hand is vulnerable to traumatic injury (Custer et al. (1999) *Vascular Surgery* 33, 567-577; Spittell and Spittell (1993) *International Journal of Cardiology* 38, 281-292), and subclinical distal ulnar artery occlusion has been reported to be prevalent in occupational workers. (Little et al. (1972) *Archives of Surgery*; Kaji et al. (1993) *Journal of Hand Surgery* 18B, 761-766). Immunohistochemistry was used to examine the vulnerable portion of the distal ulnar artery in 42 patients, ranging in age from 31 to 86 years, to determine the extent and nature of vascular disease at this location in the selected patient population. Hematoxylin and eosin staining (FIG. 1) revealed that intimal hyperplasia was common at this location. The intimal smooth muscle cells were strongly reactive for smooth muscle actin (SMA), and non-reactive for the endothelial and stem cell marker CD34 (FIG. 2). Although intimal hyperplasia was common at this site, there was no evidence of atherosclerosis. No foam cells and/or a necrotic/lipid core were observed in any of the 42 arterial segments examined. Thus, these results show that this arterial segment is resistant to the formation of atherosclerosis, despite being prone to chronic injury and routinely developing intimal hyperplasia. Further, these studies on the distal ulnar artery intima underscore several observations concerning human atherosclerosis. First, intimal hyperplasia and mechanical injury are not sufficient to cause atherosclerosis in humans. Additionally, intimal hyperplasia readily forms in atherosclerosis-resistant arteries, suggesting that there may be biochemical differences in the intimal hyperplasia that forms at distinct arterial locations, and that these differences may lead to the formation of mature atherosclerotic lesions.

Example 2

Lumican Proteoglycan is Upregulated in Pre-Atherosclerotic Lesions of Atherosclerosis-Prone Arteries Since proteoglycans of the intimal extracellular matrix have been implicated as playing a direct role in atherosclerosis, a proteomics based approach was used to determine intimal proteoglycan composition, and how this composition might vary at different sites in the circulation. Increasing evidence has pointed to a role for lumican proteoglycan (PG) in atherosclerosis. Lumican proteoglycan is synthesized by both vascular endothelial cell in a 100 kDa form (lumican-PG100), and by vascular smooth muscle cells in a 65 kDa form (lumican-PG65) (Qin et al. (2001)). Both forms of lumican PG are observed in human intima. Lumican PG has been shown to be upregulated in the vascular intima during atherosclerotic lesion formation (Archacki et al. (2003)), and to a greater extent in the pre-atherosclerotic lesions of vessels prone to develop atherosclerosis.

Figure 3:
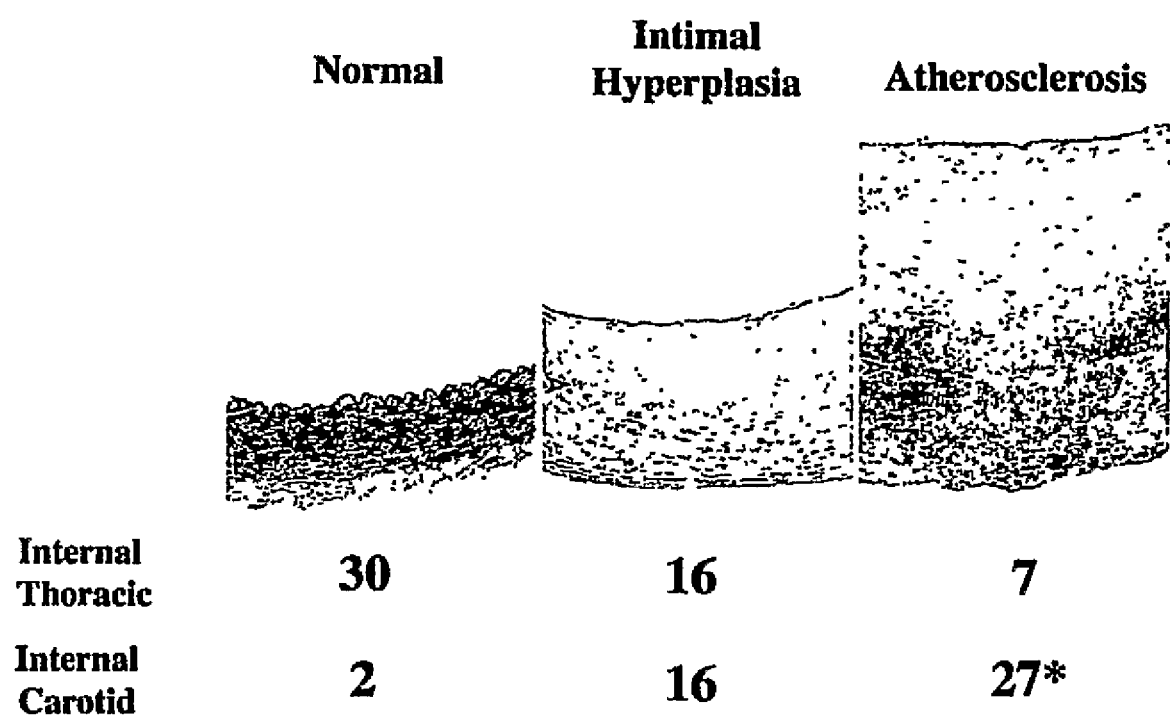
FIG. 3 shows representative histologic images of hematoxylin and eosin stained sections of internal thoracic arteries at 100× magnification. The arrowheads indicate the intima/media boundaries. The arrow indicates a developing necrotic/lipid core. The numbers indicate the number of cases for each vessel with the corresponding lesion type; *P<0.0001.

Here, a proteomics analysis was performed using both the atherosclerosis-prone internal carotid artery as well as the atherosclerosis resistant internal thoracic artery. Left internal carotid arteries, at the level of the carotid bifurcation, and/or internal thoracic arteries, at the level of bifurcation of the intercostal arteries below the second rib, were obtained from 56 randomly selected autopsies within 24 hours of death. Patients ranged in age from the $4^{th}$ to the $10^{th}$ decades of life. Cases were excluded if there was a history of prior surgery or radiation therapy involving the arterial segments. Both of these arterial segments are elastic arteries, in contrast to muscular arteries, and are thus amenable to direct comparison for differences in extracellular matrix composition. Intimal hyperplasia was defined as an intima >0.03 mm thick with or without isolated/focal foam cells. Atherosclerosis was defined as the presence of numerous foam cells and/or a necrotic/lipid core. Histological analysis was used to classify the arterial segments based on lesion type (FIG. 3). Briefly, a representative cross section was fixed in 10% buffered formalin, processed with a paraffin embedding procedure, and used to generate hematoxylin-and-eosin-stained histological slides. The remainder of the tissue was stored for proteomic analysis. FIG. 3 shows representative histologic images of hematoxylin and eosin stained sections of internal thoracic arteries at 100× magnification. This analysis revealed that 27 of 45 left internal carotid arteries developed atherosclerotic lesions, with 16 of the remaining 18 cases showing intimal hyperplasia. In contrast, atherosclerosis was present in the internal thoracic arteries of only 7 of 53 patients, confirming the atherosclerosis resistance of this site. Of the 46 patients without atherosclerosis in the internal thoracic arteries, the histological staining showed that 16 had developed significant eccentric intimal hyperplasia. The extracellular proteoglycan composition of the intimal proteoglycan of the intimal hyperplasia from the 16 left internal carotid arteries was compared to that of the intimal hyperplasia from 16 pairs of internal thoracic arteries. There was not a statistically significant difference between the two groups with regard to age, gender, macrophage density or the presence of focal foam cells (Talusan et al. (2005) *Molecular and Cellular Proteomics* 4, 1350-1357). Thus, this data shows that like the distal ulnar artery, the internal thoracic artery routinely develops intimal hyperplasia, yet remains relatively resistant to the formation of atherosclerosis.

Figures 4A, 4B:
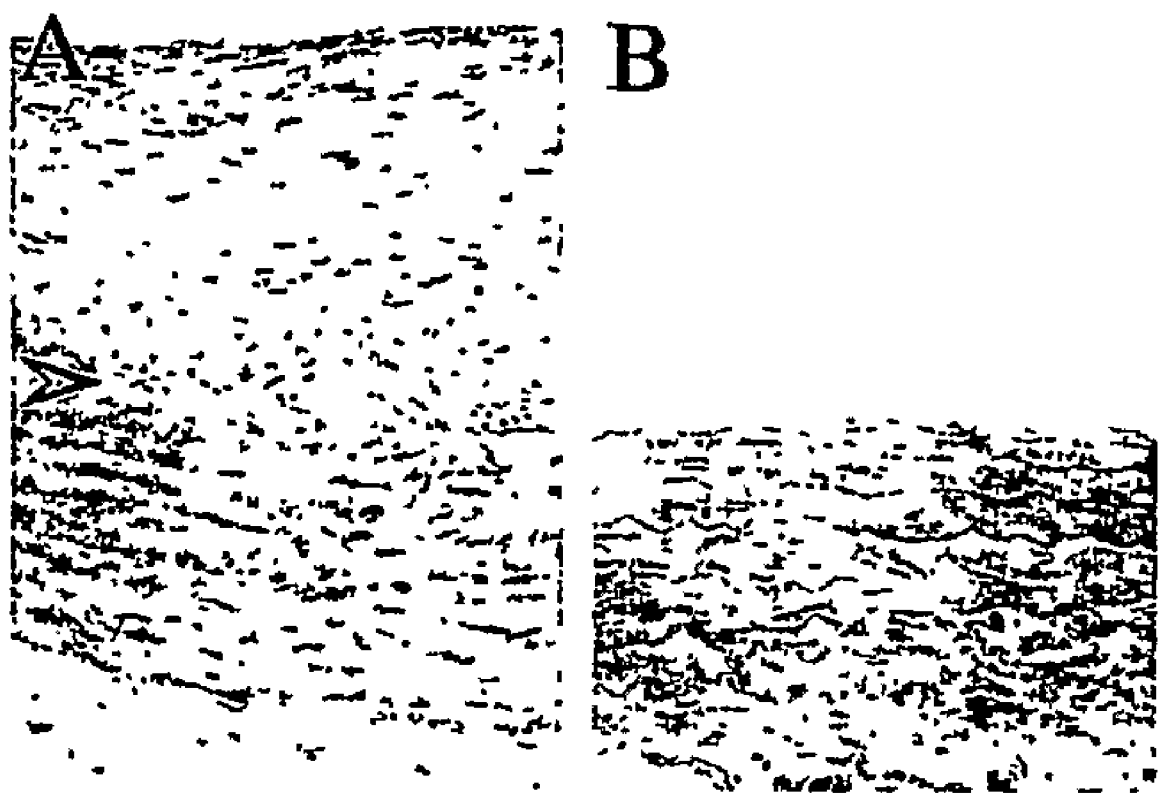
FIG. 4 shows a representative section of an internal thoracic artery stained with hematoxylin and eosin at 200× magnification (A) before and (B) after removal of the thickened intima. The arrowhead indicates the level of the intima/media boundary.

Subsequently, the extracellular proteoglycan composition of the intimal hyperplasia from these 16 left internal carotid arteries was compared to that of the intimal hyperplasia from the 16 pairs of internal thoracic arteries. To compensate for the 2-fold larger size of the internal carotid artery and allow for similar quantities of protein for analysis, both internal thoracic arteries from a given patient were processed together. The two groups were matched in terms of patient age, gender, and macrophage density, and the presence of focal foam cells. There was an enhanced ratio of intima thickness to media thickness in the internal carotid arteries compared to the internal thoracic arteries (0.9+/−0.7 vs. 0.4+/−0.3). For each arterial segment, the thickened intima was carefully removed. FIG. 4 shows a representative section of a hematoxylin and eosin stained internal thoracic artery before and after removal of thickened intima. Following removal of the intima, the proteoglycans were extracted and isolated, and then analyzed by liquid chromatography tandem mass spectrometry. Mass spectral intensities for peptides from the more frequently occurring proteoglycans were compared. Every MS/MS spectra obtained was used to search the human NCI database (130,741 protein entries when searched) using Sequest version 27.9. The database was searched using no enzyme specificity and a precursor ion mass accuracy of +/−1 Da, allowing for the differential modification of Met (+16 Da, oxidation) and Cys (+71, monoacryliamide) and for up to three missed cleavages sites. After the initial search, non-tryptic peptide matches were discarded. The remaining matches were manually inspected for quality. Those matches typically considered true matches had Cn scores of at least 0.1 and Xcorr values of 2.0 or greater for +1 and +2 charged peptides. A particular proteoglycan was considered to be present only if 2 or more such high quality peptides were identified in at least one of the initial preparations. Initial preliminary assessments of the relative quanities of the various proteoglycans were based on the MS intensities of specific peptides observed in most or all of the samples. These peptides were as follows: versican (SEQ ID NO:1 LLASDAGLYR, SEQ ID NO:2 LATVGELQAAWR, and SEQ ID NO:3 ETTVLVAQNGNIK), biglycan (SEQ ID NO:4 LGLGHNQIR), decorin (SEQ ID NO:5 SSGIENGAFQGMK), perlecan (SEQ ID NO:6 SIEYSPQLEDAGSR and SEQ ID NO:7 LEGDTLIIPR), lumican (SEQ ID NO:8 SLEDLQLIHNK and SEQ ID NO:9 LKEDAVSAAFK), and fibromodulin (SEQ ID NO:10 IPPVNTNLENLYLLQGNR and SEQ ID NO:11 YLPFVPSR). In cases where more than one commonly occurring peptide was used for a particular proteoglycan, the signal intensities for the peptides were averaged.

The results of the mass spectral analysis (FIG. 5) were consistent with previous immunohistochemistty studies (Guitierrez et al. (1997) *Cardiovascular Pathology* 6, 271-278; Kolodgie et al. (2002) *Arteriosclerosis Thrombosis and Vascular Biology* 22, 1642-1648; Lin et al. (1998) *Cardiovascular Pathlology* 15, 1233-1247; O'Brien et al. (1998) *Circulation* 98, 519-527; Chung et al. (2002) *Journal of the American College of Cardiology* 40, 2072-2081; Murdoch et al. (1993) *Virchows Archives A Pathology Anatomy* 423, 237-

Figure 5A:
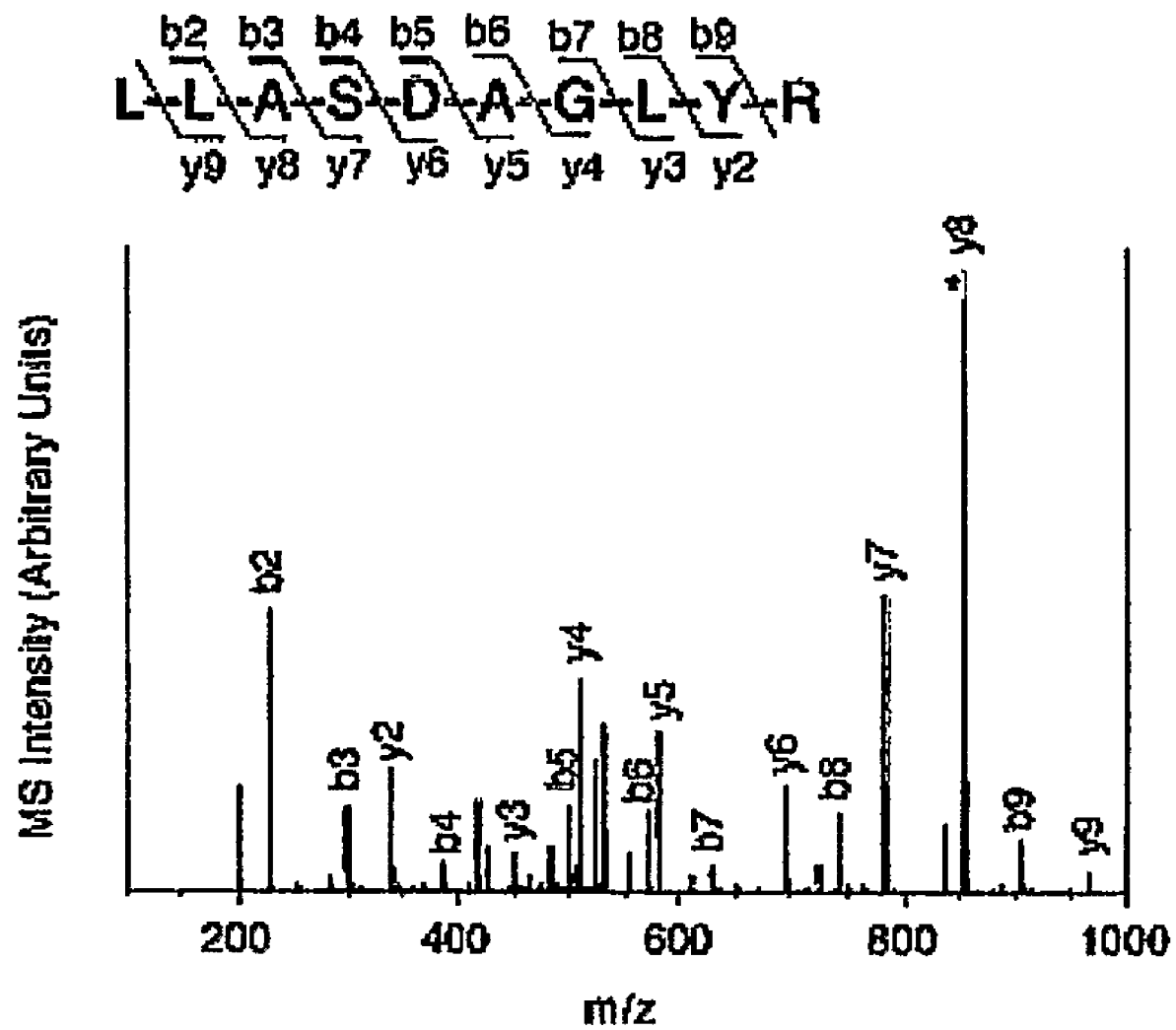
FIG. 5 depicts the results of representative tandem mass spectra showing the identification of (A) versican (SEQ ID NO:1), (B) perlecan (SEQ ID NO:6), (C) aggrecan (SEQ ID NO:12), and (D) lumican (SEQ ID NO:8). Some peaks (*) have been scaled by 50% for presentation. The y-axes are arbitrary units in a linear scale starting at zero.
Figure 5B:
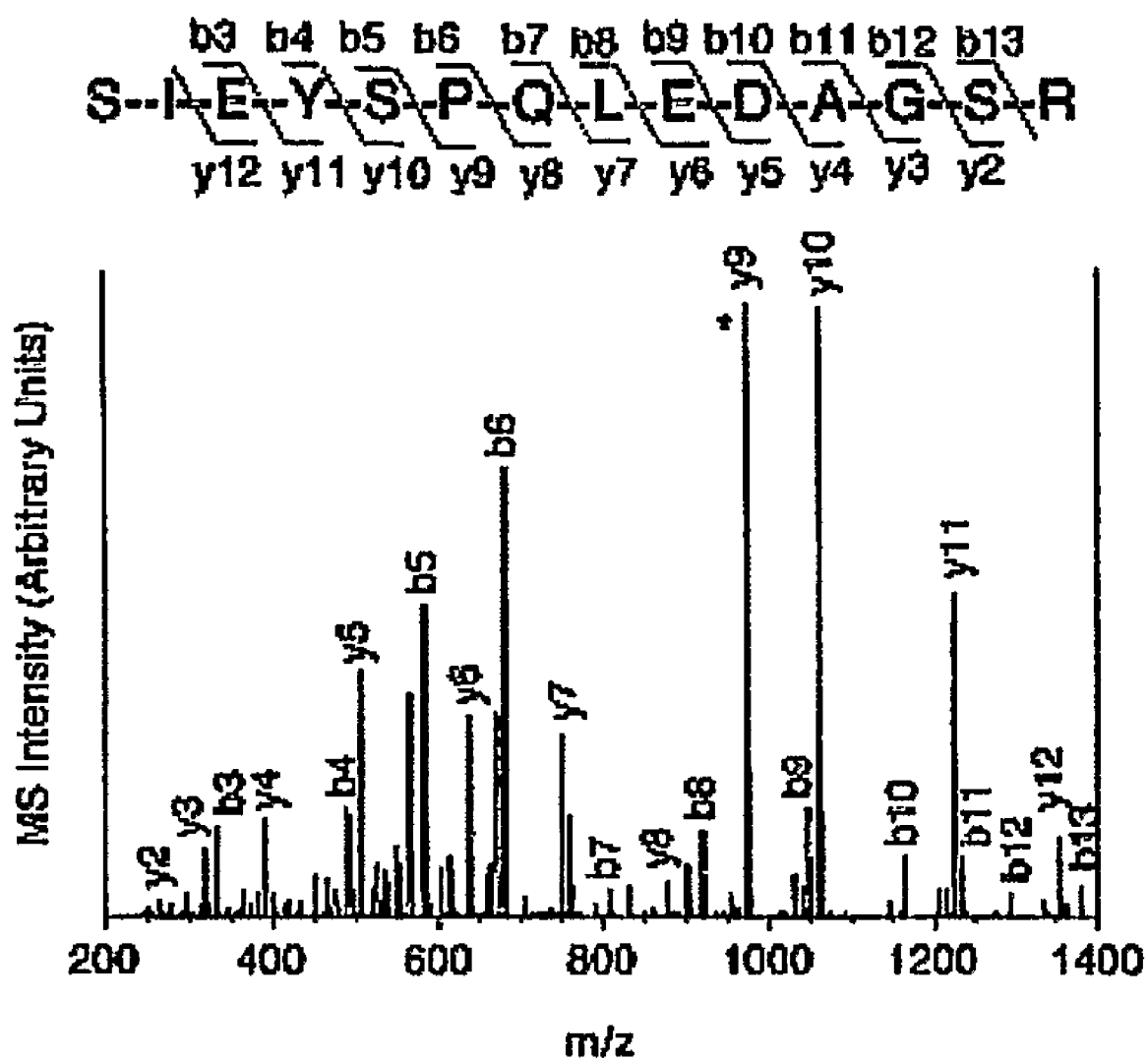
Figure 5C:
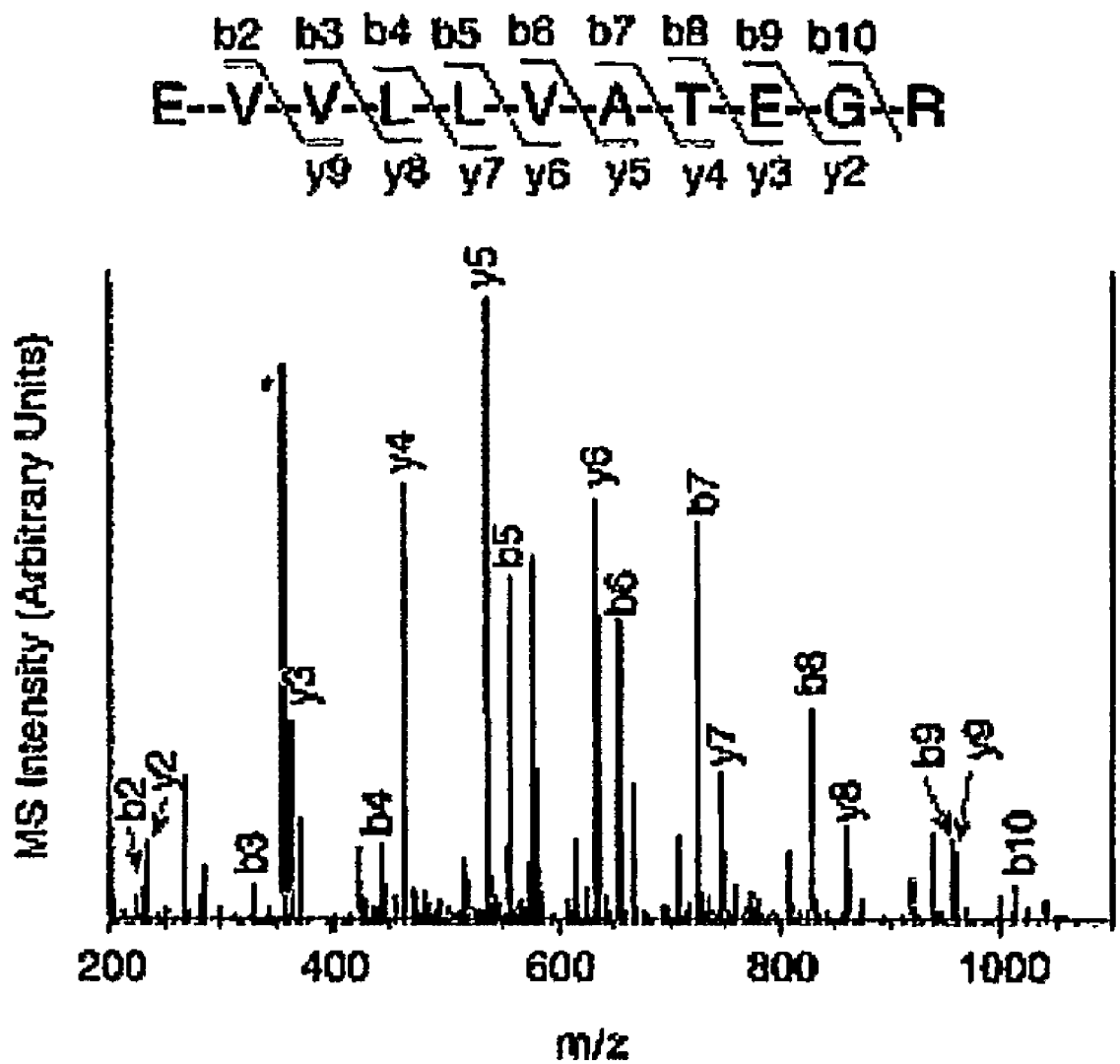

242); versican, biglycan, and perlecan were detected in the intimal extracts from nearly all of the vessels examined (Table 1 and FIG. 5).

TABLE 1

Human Intimal Proteoglycans Identified by Mass Spectometry

| | Internal Carotid | | | Internal Thoracic | | |
|---|---|---|---|---|---|---|
| | Frequency | No. of Peptides | Sequence Coverage | Frequency | No. of Peptides | Sequence Coverage |
| Large Extracellular PGs | | | | | | |
| Versican | 100% | 4-17 | 1-5% | 100% | 5-11 | 2-4% |
| Aggrecan | 13% | 1-8 | 0.3-2% | 38% | 1-6 | 0.5-2% |
| Basement Membrane PGs | | | | | | |
| Perlecan | 94% | 3-22 | 1-6% | 100% | 3-27 | 1-8% |
| Class I SLR PGs | | | | | | |
| Biglycan | 100% | 5-15 | 16-52% | 100% | 4-15 | 11-51% |
| Decorin | 94% | 1-5 | 4-20% | 88% | 1-7 | 4-22% |
| Class II SLR PGs | | | | | | |
| Fibromodulin | 88% | 1-4 | 5-11% | 75% | 1-4 | 2-11% |
| Lumican | 81% | 1-8 | 3-31% | 56% | 2-6 | 6-25% |
| Prolargin/PRELP | 56% | 2-7 | 5-20% | 44% | 1-4 | 3-11% |

The greatest numbers of peptides were routinely observed for these three proteoglycans, suggesting they are the three major proteoglycans expressed in intimal hyperplasia. Here, lumican was detected in intimal hyperplasia in most of the specimens analyzed (Table 1 and FIG. 5). These results are consistent with previous data indicating that immunoreactivity corresponding to the class II SRL proteoglycan lumican has been observed both in atherosclerotic lesions and in intimal hyperplasia (Onda et al. (2002)). Decorin was also observed in the pre-atherosclerotic lesions. Further, the large extracellular proteoglycan aggrecan, and the class II SLR proteoglycans fibromodulin and prolargin/PRELP were detected using the foregoing mass spectometry technique. These proteogylcans are not previously known to occur in human intimal hyperplasia.

To assess for difference in the quantities of these proteoglycans expressed, mass spectral intensities for peptides from the more frequently occurring proteoglycans were compared (FIG. 6). In the analysis, the signaling intensities are normalized to the total amount of intimal protein extracted. There was not a statistically significant difference in the signal intensities for versican, biglycan, and fibromodlulin in the internal carotid arteries (FIG. 6 A, B, C). However, there was a statistically significant (P<0.01) enhancement in the signaling intensities for lumican in the atherosclerosis-prone internal carotid artery compared with those from the atherosclerosis-resistant internal thoracic artery (FIG. 6D).

Figure 7A:
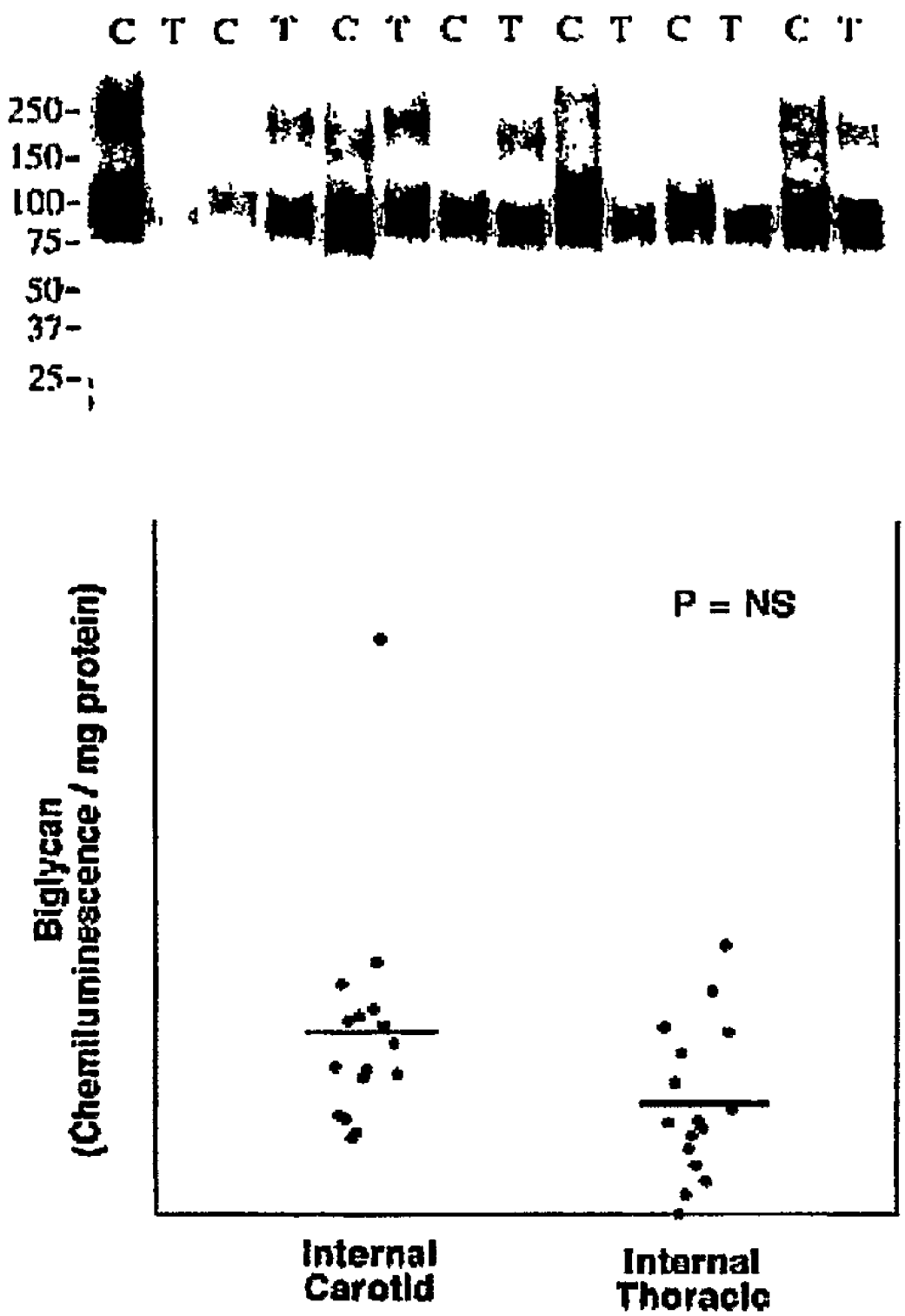
FIG. 7 shows representative immunoblots for (A) biglycan, (B) fibromodulin and (C) lumican, with alternating internal carotid "C" and internal thoracic "T" arteries. The scales to the left indicate the molecular mass markers in kDa. The bottom panels depict the quantitation of the chemiluminescence signals, which have been normalized to the total amount of intimal protein extracted. The horizontal bars indicate the mean values. The y-axes are arbitrary units in a linear scale starting at zero.
Figure 7B:
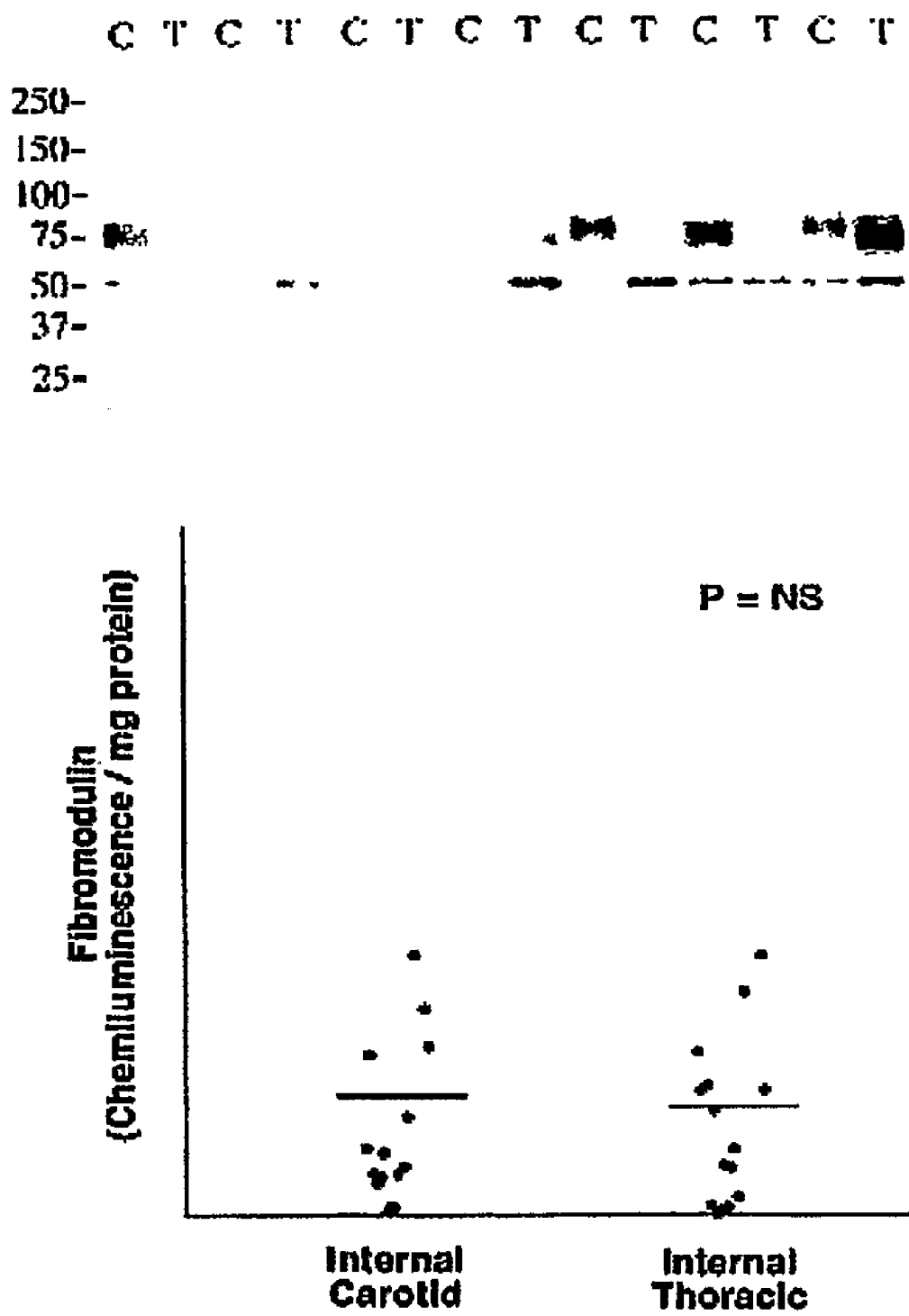
Figure 7C:
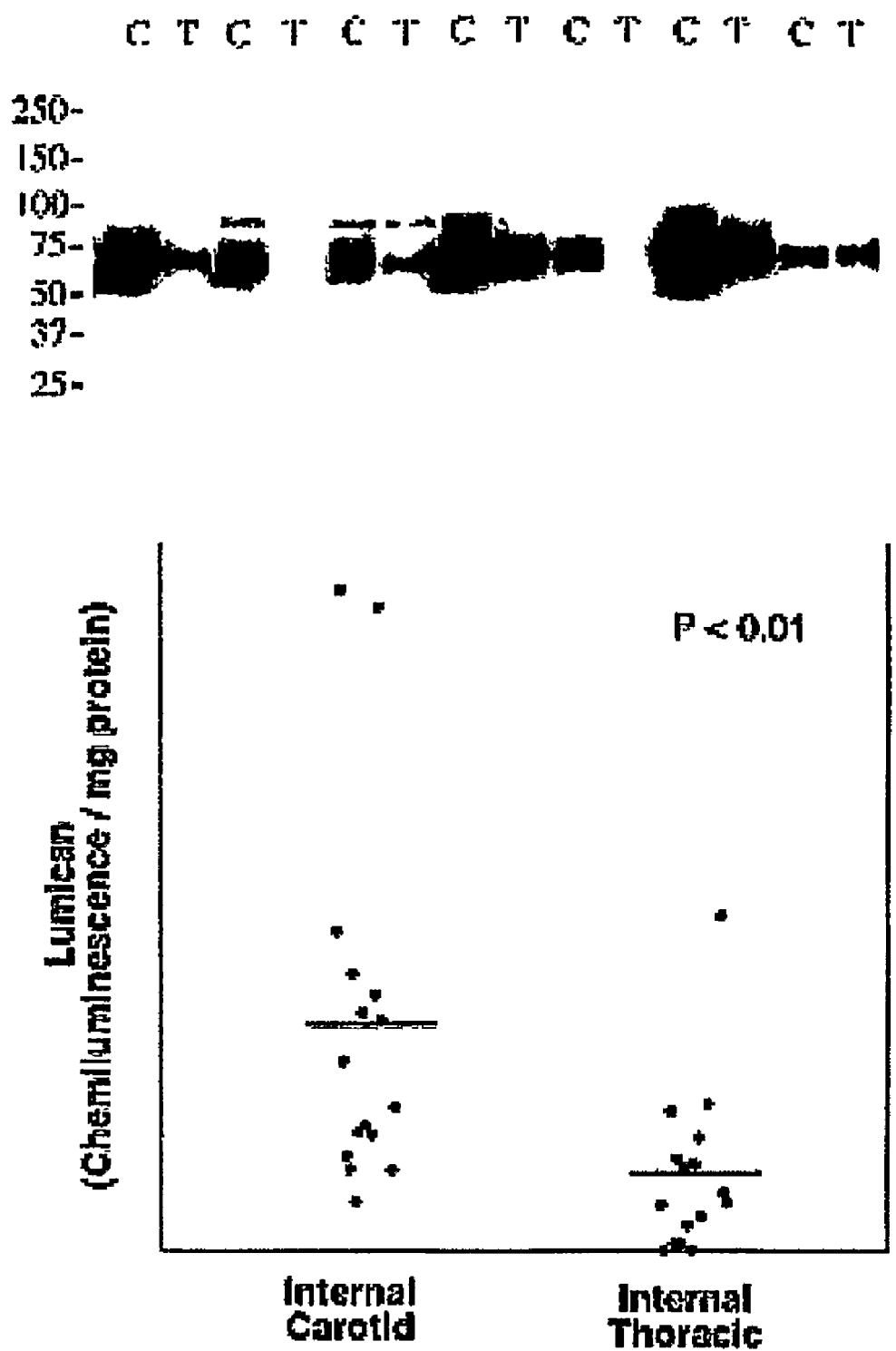

To confirm that there is enhanced deposition of lumican in the atherosclerosis-prone artery, immunoblotting for selected proteoglycans was performed on these samples of isolated proteoglycans (FIG. 7). By immunoblot analysis, biglycan is present as two distinct forms with apparent masses of ~100 kDa and ~250 kDa (FIG. 7A). These two forms of biglycan have been observed previously in tissues and cultured vascular cells (Plaas et al. (2001) Glycobiology 11, 779-790; Jarvelainen et al. (1991) Journal of Biological Chemistry 266, 23274-23281). Quantitation of the total biglycan present by immunoblotting revealed no significant difference between the atherosclerosis-prone and atherosclerosis-resistant arteries, consistent with the analysis of mass spectral intensities. By immunoblotting, fibromodulin is present as both a sharp band with an apparent mass of ~50 kDa and a more diffuse band with an apparent mass of ~80 kDa (FIG. 7B). The lower band may represent a tyrosine sulfated core protein lacking carbohydrate modification, and the upper band likely represents a form with carbohydrate modifications (Sztrolovics et al. (1999) Spine). Again consistent with the analyses of the mass spectral intensities, there was no difference in the amount of fibromodulin present in intima from the two arterial locations. Immunoblotting for lumican (FIG. 7C) revealed multiple diffuse bands predominantly from 60-100 kDa, indicative of the proteoglycan forms of lumican (Sztrolovics et al. (1999)), Funderburgh et al. (1991), Dolhnikoff et al. (1998); Qin et al. (2001)). Consistent with the analysis of the mass spectral intensities, there was significantly (P<0.01) more lumican present in the intima of the atherosclerosis-prone internal carotid artery than in the atherosclerosis-resistant internal thoracic artery, with the mean value elevated by approximately 3 fold.

Taken together, these data show that a comparison of the pre-atherosclerotic intimal hyperplasia of the atherosclerosis prone internal carotid artery with that of the atherosclerosis resistant internal thoracic artery revealed the major difference in the extracellular proteoglycan composition between the two sites to be the enhanced deposition of lumican proteoglycan in the intima of the atherosclerosis prone artery.

Example 3

Vascular Intimal Lumican is a Keratan Sulfate Proteoglycan

Figure 8:
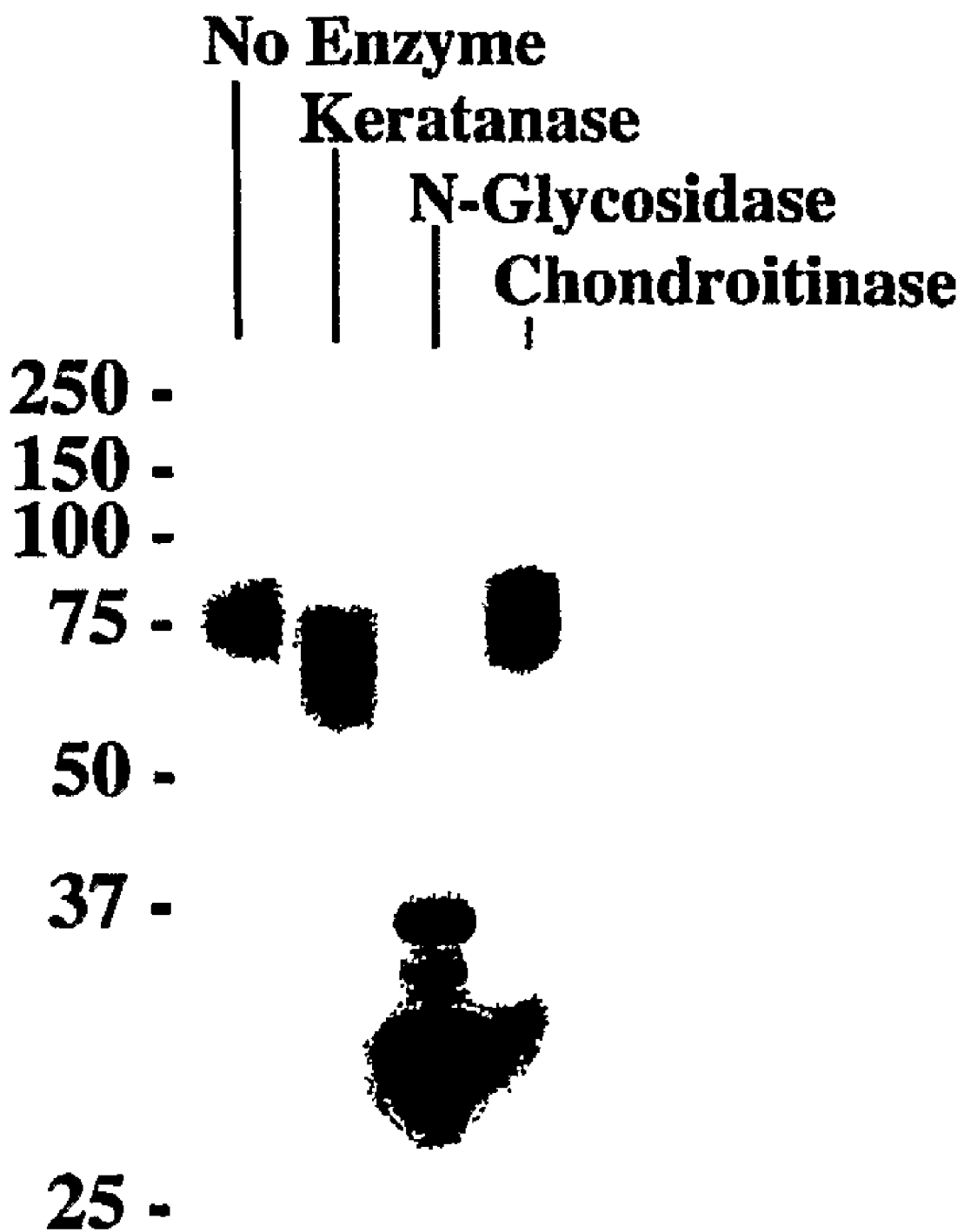
FIG. 8 illustrates that vascular intimal lumican is a keratan sulfate proteoglycan. Proteoglycans isolated from human intima were subjected to enzymatic digestion followed by Western blotting for Lumican. Labels above the lanes indicate the respective treatments.

The sensitivity of human vascular intimal lumican proteoglycan to enzymatic digestion with various glycosaminoglycan (GAG)-degrading enzymes was examined. Proteoglycans from human common carotid intima were isolated as described in the literature (Talusan et al. (2005)). The isolated proteoglycans were then subjected to digestion with keratanase, to digest keratan sulfate, chondroitinase, to digest chondroitin sulfate, and N-glycosidase, which completely digests carbohydrates linked to asparagine residues. Proteoglycans were isolated from the intima of common carotid arteries and then dialyzed against 50 mM Tris pH 7.4 to remove excess NaCl. The proteoglycans were then digested with 5 uL of chondroitinase (Seikagaku America), keratanase (Seikagaku America), N-glycosidase-F (Calbiochem), or no enzyme. The samples were analyzed by immunoblotting for lumican as described in the literature (Talusan et al. (2005)). The GAG side chains in lumican were sensitive to N-glycosidase digestion, which reduced the apparent mass of the ~75 kDa intimal lumican proteoglycan to that of the isolated core protein 30-37 kDa (FIG. 8). The intimal lumican proteoglycan was also sensitive to keratanase digestion, which caused the apparent mass to decrease from ~75 kDa to ~60 kDa, establishing that human intimal lumican proteoglycan contains intact keratan sulfate. This is in contrast to the previously reported ubiquitously expressed 55 kDa lumican glycoprotein (Lumican-P55), which shows no sensitivity to keratanse enzymatic digestion (Funderburgh et al. (1991)). This data demonstrates that the proteoglycan form of lumican can exist outside of cornea and cartilage, where it had been previously described. Further the data implicates this lumican proteoglycan as playing an important role in atherosclerotic lesion formation.

Example 4

Aggrecan is an Intimal Proteoglycan

Figure 9:
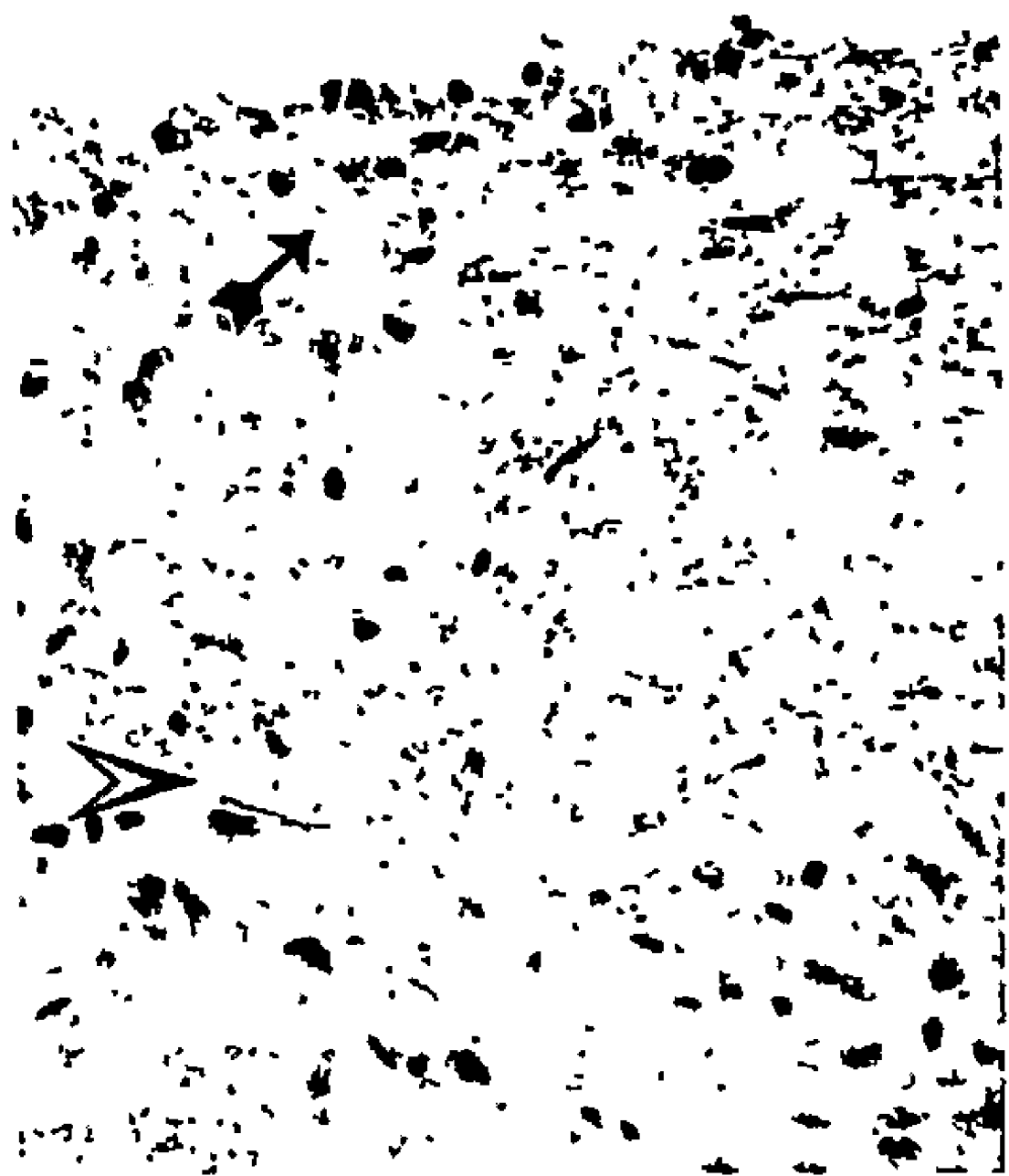
FIG. 9 shows immunohistochemical staining for aggrecan in an internal carotid artery with intimal hyperplasia at 400× magnification. The arrowhead indicates the intima/media boundary; the arrow indicates aggrecan immunoreactivity in the inner intima.

The inner (sub-endothelial) zone of intimal hyperplasia is known to be particularly rich in proteoglycans (Stary et al. (1992) *Circulation* 85, 391-405), although the presence of aggrecan in human intimal hyperplasia has not been previously described. Results of the mass spectral analysis, described above, revealed the presence of aggrecan in human intimal hyperplasia. To verify the location of aggrecan in human intima, immunohistochemistry for aggrecan was performed. Immunoreactivity for aggrecan was observed predominantly in the inner intima, with very faint immunoreactivity in the deeper intima and media (FIG. 9, arrow). Thus, immunohistochemical staining confirms that in addition to versican, aggrecan is a large extracellular proteoglycan that contributes to the structure of the matrix in the proteoglycan-rich zone of the inner intima. Due to the large size of aggrecan, and the large number of glycosaminoglycan modification sites, aggrecan has the potential to have the greatest affinity for lipoproteins of all of the intimal proteoglycans. This data indicates that there appears to be enhanced deposition of aggrecan proteoglycan in the intima of the atherosclerosis-prone arteries.

Example 5

Figure 10:
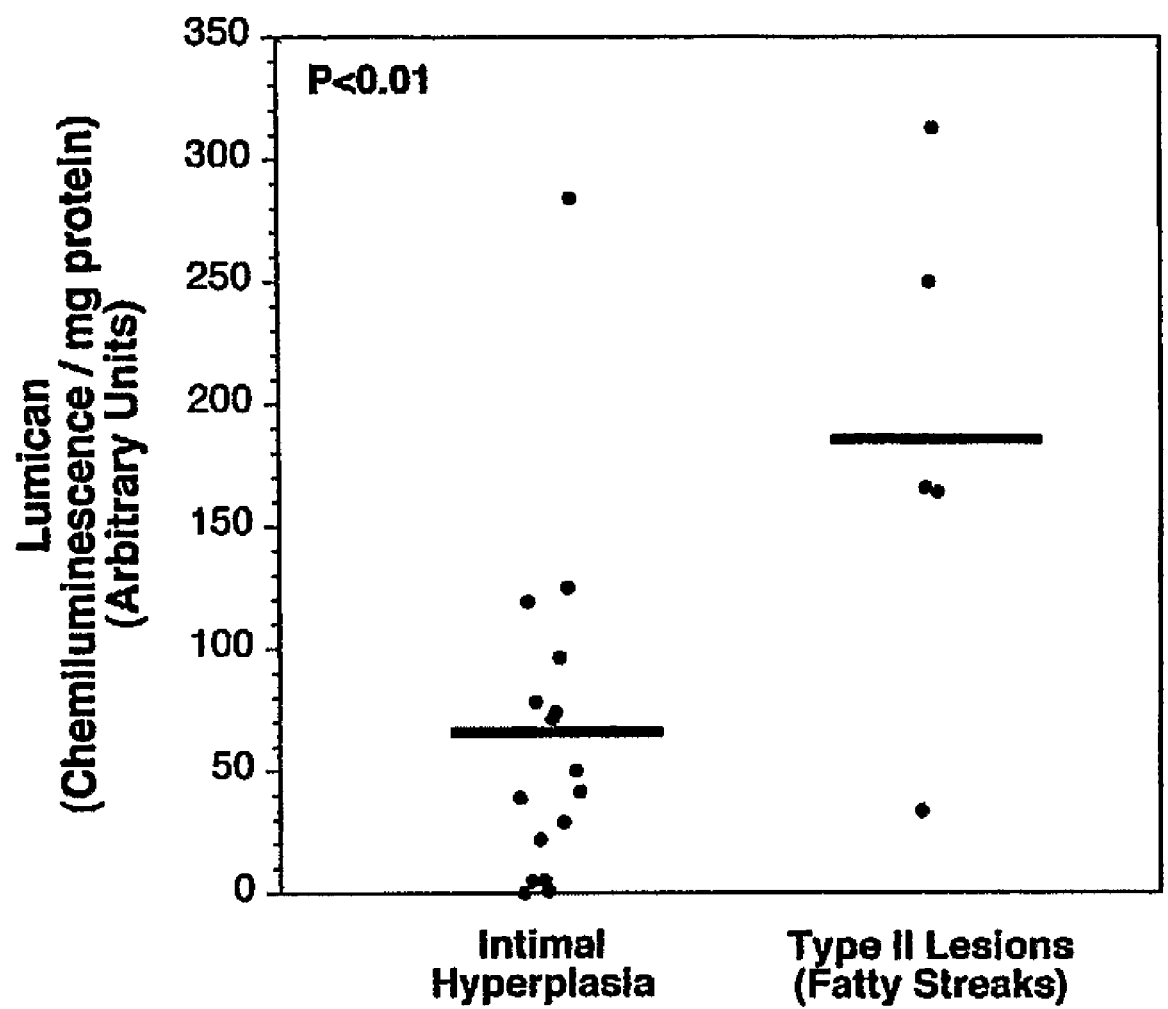
FIG. 10 shows by immunoblot that lumican is up-regulated in fatty streaks compared with intimal hyperplasia.

Deposition of Lumican Proteoglycan Correlates with Lesion Type in an Atherosclerosis Resistant Artery Proteoglycan extraction and analysis was performed on internal thoracic arteries from 5 patients in which the vessels showed diffuse foam cell formation, Type II Fatty Streaks. Immunoblotting was used to assess the lumican content of these fatty streaks (FIG. 10). Lumican levels were found to be significantly greater in Type II fatty streaks than in intimal hyperplasia at this site in internal thoracic arteries (P<0.01). There was no such increase in versican, biglycan or fibromodulin upon comparing fatty streaks with intimal hyperplasia in these vessels, indicating that this enhancement in lumican deposition with initial progression of lesion type is specific to lumican. This data reinforces that lumican is the extracellular proteoglycan most closely associated with atherosclerotic lesion development in humans.

Example 6

Stress Levels of Hydrogen Peroxide Stimulate the Upregulation of Lumican Proteoglycan by Human Endothelial Cells Previously, it was determined through mass spectral proteoglycan profiling of the conditioned media from cultured human umbilical vein endothelial cells (HUVECs) that in addition to perlecan and biglycan, two extracellular proteoglycans that were known to be generated by human endothelail cells, lumican was present as the only keratan sulfate proteoglycan in the conditioned medium of the HUVEC cultures (Talusan et al. (2005)).

Figure 11:
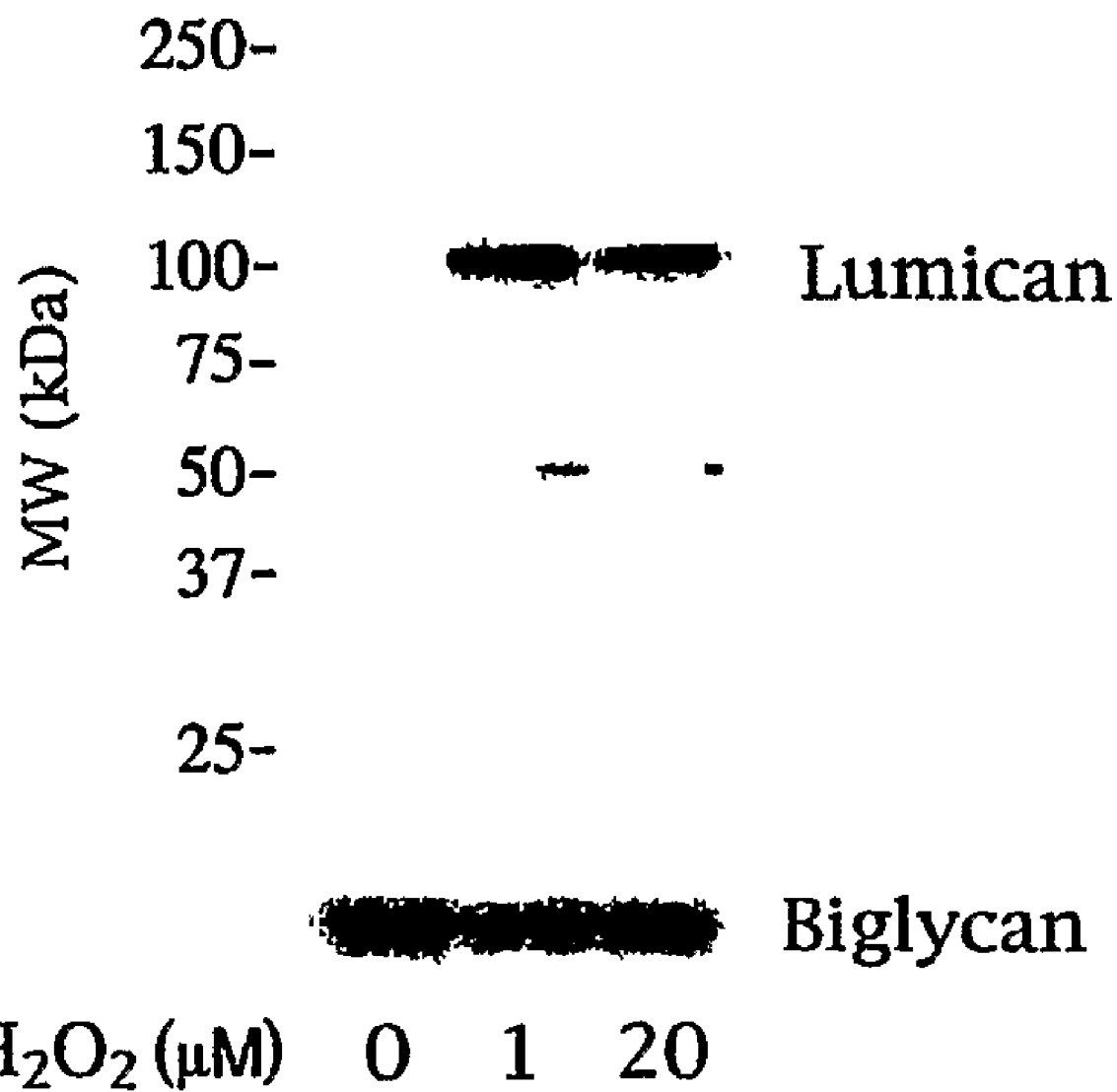
FIG. 11 shows the upregulation of lumican proteoglycan in endothelial cells by physiologic proatherogenic levels of $H_2O_2$. HUVECs were treated with the indicated concentrations of $H_2O_2$ for 5 hours. The cells were harvested and the proteoglycans isolated and analyzed by Western blotting for lumican and biglycan.

Since lumican proteoglycan is deposited at enhanced levels in atherosclerosis-prone arteries, it is possible that lumican proteoglycan is generated by cultured human umbilical vein endothelial cells (HUVECs). The production of lumican proteoglycan by cultured human umbilical vein endothelial cells (HUVECs) was examined in vitro. Confluent HUVECs in complete media with serum and growth supplements were treated with a single bolus addition of varying concentrations of $H_2O_2$. After 5 hr the cells were washed and harvested as described previously (Kattapuram et al. (2005) *Journal of Biological Chemnistry* 280, 15340-15347). The proteoglycans were then extracted, isolated and analyzed by immunoblotting for lumican and biglycan. Under resting conditions, HUVECs produce low levels of lumican-PG100. However, upon treatment of the cells with physiologic levels of $H_2O_2$, a proatherogenic stimulus, there is substantial upregulation of Lumican-PG100 (FIG. 11). In contrast, there is no upregulation of biglycan with this treatment. This data provides a mechanistic rationale for the observation that lumican proteoglycan, and not biglycan, is upregulated in atherosclerosis-prone arteries as compared with atherosclerosis-resistant arteries.

Example 7

Lumican Proteoglycan in a Mouse Model of Atherosclerosis

Figure 12:
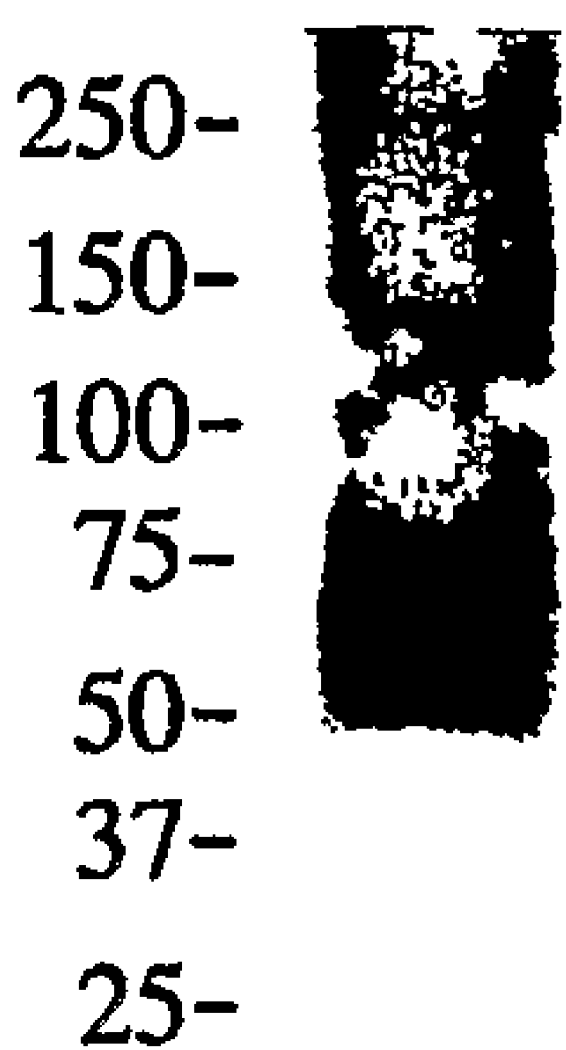
FIG. 12 shows the results of an immunoblot for lumican in the diseased aorta from a lipid-fed ApoE-deficient mouse.

An apolipoprotein E (ApoE$^{-/-}$) mouse model of atherosclerosis was used to determine the presence of lumican proteoglycan. Diseased aortas from apolipoprotein E (ApoE$^{-/-}$) mice fed a high-fat diet were subjected to immunoblot-analysis for lumican (FIG. 12). The apolipoprotein E (ApoE$^{-/-}$) mouse atherosclerotic lesions were found to contain high levels of lumican based on the presence of a diffuse band between 50 and 75 kDa, similar to that observed in human intima (FIG. 12). Thus, as with human atherosclerosis, lumican proteoglycan is an intimal component in mouse models of atherosclerosis.

I claim:

1. A method of reducing atheroma formation in a subject in need thereof, comprising:
administering an effective amount of an agent that inhibits an enzyme required for lumican proteoglycan synthesis to the subject, wherein the enzyme is a sulfotransferase, and the agent is selected from the group consisting of a triclosan, an alkylamine, a 2,6-Dichloro-4-nitrophenol, and an antibody that specifically interferes with the activity of a sulfotransferase, thereby reducing atheroma formation in the subject.

2. The method of claim 1, wherein atheroma formation is inhibited.

3. The method of claim 1, wherein the agent is administered directly to a blood vessel of the subject.

4. The method of claim 1, wherein the agent inhibits the synthesis of lumican proteoglycan keratan sulfate side chains.

5. The method of claim 1, wherein the sulfotransferase is N-acetylglucosamine 6-O-sulfotransferase or keratan sulfate galactose-sulfotransferase.

6. A method of treating an atherosclerotic lesion in a subject in need thereof, comprising:
administering an effective amount of an agent that inhibits an enzyme required for lumican proteoglycan synthesis to the subject, wherein the enzyme is a sulfotransferase, and the agent is selected from the group consisting of a triclosan, an alkylamine, a 2,6-Dichloro-4-nitrophenol, and an antibody that specifically interferes with the activity of a sulfotransferase, thereby treating the atherosclerotic lesion in the subject.

7. The method of claim 6, wherein the atherosclerotic lesion is eradicated.

8. The method of claim 6, wherein the agent is administered directly to a blood vessel of the subject.

9. The method of claim 6, wherein the agent inhibits the synthesis of lumican proteoglycan keratan sulfate side chains.

10. The method of claim 6, wherein the sulfotransferase is N-acetylglucosamine 6-O-sulfotransferase or keratan sulfate galactose-sulfotransferase.

11. A kit for treating an atherosclerotic lesion comprising a) an effective amount of an agent that inhibits an enzyme required for lumican proteoglycan synthesis, wherein the enzyme is a sulfotransferase, and the agent is selected from the group consisting of a triclosan, an alkylamine, a 2,6-Dichloro-4-nitrophenol, and an antibody that specifically interferes with the activity of a sulfotransferase, wherein the agent reduces lumican proteoglycan in the lesion, and b) instructions for use thereof.

12. The kit of claim 11, which comprises a packaged pharmaceutical comprising: a) an effective amount of an agent that reduces the amount of lumican proteoglycan in an atherosclerotic lesion by inhibiting an enzyme required for lumican proteoglycan synthesis, wherein the enzyme is a sulfotransferase, and the agent is selected from the group consisting of a triclosan, an alkylamine, a 2,6-Dichloro-4-nitrophenol, and an antibody that specifically interferes with the activity of a sulfotransferase, and b) instructions for using said agent to treat said atherosclerotic lesion.

* * * * *